(12) United States Patent
Wang et al.

(10) Patent No.: US 12,280,157 B2
(45) Date of Patent: Apr. 22, 2025

(54) COMPOSITIONS AND METHODS FOR INHIBITING POST-SURGICAL ADHESIONS

(71) Applicant: The University of North Carolina at Chapel Hill, Chapel Hill, NC (US)

(72) Inventors: Andrew Wang, Chapel Hill, NC (US); Yu Mi, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 828 days.

(21) Appl. No.: 17/428,843

(22) PCT Filed: Feb. 6, 2020

(86) PCT No.: PCT/US2020/017021
§ 371 (c)(1),
(2) Date: Aug. 5, 2021

(87) PCT Pub. No.: WO2020/163601
PCT Pub. Date: Aug. 13, 2020

(65) Prior Publication Data
US 2022/0125736 A1    Apr. 28, 2022

Related U.S. Application Data

(60) Provisional application No. 62/802,033, filed on Feb. 6, 2019.

(51) Int. Cl.
| | | |
|---|---|---|
| *A61K 9/51* | (2006.01) | |
| *A61K 31/573* | (2006.01) | |
| *A61P 41/00* | (2006.01) | |
| *B82Y 5/00* | (2011.01) | |

(52) U.S. Cl.
CPC ............ *A61K 9/51* (2013.01); *A61K 31/573* (2013.01); *A61P 41/00* (2018.01); *B82Y 5/00* (2013.01)

(58) Field of Classification Search
CPC ...... A61K 9/51; A61K 31/573; A61K 9/5146; A61K 9/5153; A61K 45/00; A61P 41/00; B82Y 5/00; A61L 2300/43; A61L 2400/12; A61L 2430/40; A61L 31/129; A61L 31/148; A61L 31/16
See application file for complete search history.

(56) References Cited

U.S. PATENT DOCUMENTS

| | | | |
|---|---|---|---|
| 8,067,031 B2 * | 11/2011 | Daniloff | A61K 9/1075 |
| | | | 523/105 |
| 2010/0068261 A1 | 3/2010 | Tamarkin et al. | |
| 2011/0143993 A1 | 6/2011 | Langer et al. | |
| 2011/0275573 A1 | 11/2011 | Dahan et al. | |
| 2015/0024376 A1 | 1/2015 | Ozanich | |
| 2016/0091489 A1 | 3/2016 | Fan et al. | |
| 2016/0122390 A1 * | 5/2016 | Popel | A61P 37/06 |
| | | | 435/375 |
| 2016/0339147 A1 | 11/2016 | Cauchon | |

FOREIGN PATENT DOCUMENTS

| | | | |
|---|---|---|---|
| CN | 101080246 | 11/2007 | |
| CN | 102448442 | 5/2012 | |
| EP | 3205336 | 8/2017 | |
| EP | 3 406 270 A1 | 11/2018 | |
| WO | WO 95/33410 A1 | 12/1995 | |
| WO | WO 2010/100506 A2 | 9/2010 | |
| WO | WO 2015/019109 | 2/2015 | |
| WO | WO-2018152444 A1 * | 8/2018 | ............ A61K 9/06 |

OTHER PUBLICATIONS

Addressing Unmet Clinical Needs with UV Bioadhesives, Biomacromolecules, 2017 (Year: 2017).*
Buwalda, S.J. et al., "Hydrogels for therapeutic delivery: current developments and future directions," Biomacromolecules, 18:316-330, (2017).
Lee, J.H. et al., "Tissue anti-adhesion potential of ibuprofen-loaded PLLA-PEG diblock copolymer films," Biomaterials, 26:671-678, (2005).
WIPO Application No. PCT/US2020/017021, PCT International Search Report and Written Opinion of the International Searching Authority mailed Sep. 21, 2020.
Xie, Q. et al., "Fabrication of core-shell PEI/pBMP2-PLGA Electrospum scaffold for gene delivery to periodontal ligament stem cells," Stem Cells International, 2016(5385137):1-11, (2016).
EP Application No. 20752091.7, Extended European Search Report mailed Oct. 11, 2022.

* cited by examiner

*Primary Examiner* — Robert A Wax
*Assistant Examiner* — John Seungjai Kwon
(74) *Attorney, Agent, or Firm* — Alston & Bird LLP

(57) ABSTRACT

In one aspect, methods are described herein employing particle compositions operable to form composite membrane for inhibition of post-surgical adhesions. Briefly, a method of treating a surgical site comprises contacting the surgical site with a particle formulation comprising targeting particles and scaffolding particles. The targeting particles and scaffolding particles are crosslinked to provide a composite membrane at the surgical site, wherein formation of post-surgical adhesions are inhibited by the composite membrane.

17 Claims, 31 Drawing Sheets
Specification includes a Sequence Listing.

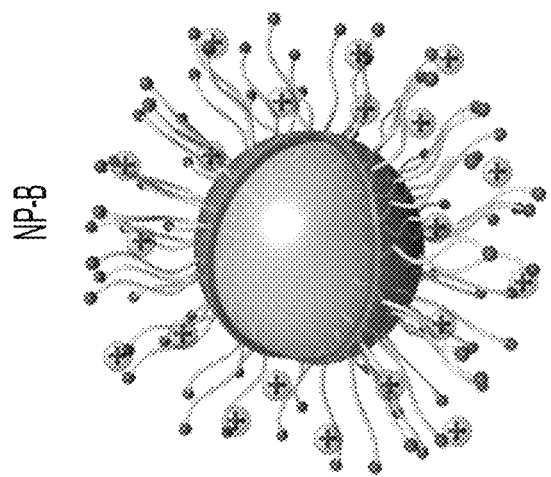
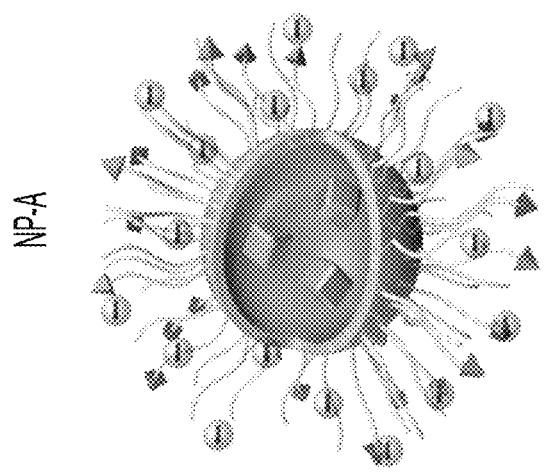
Fig. 1A

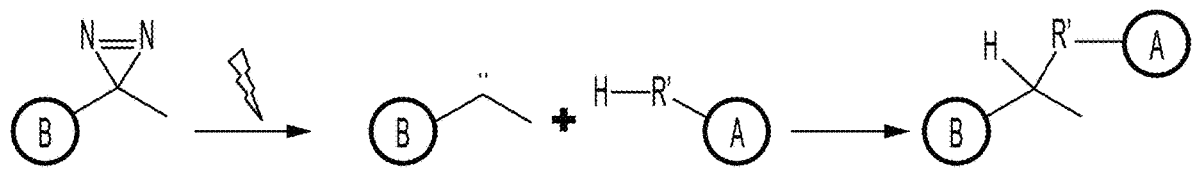
Fig. 2A
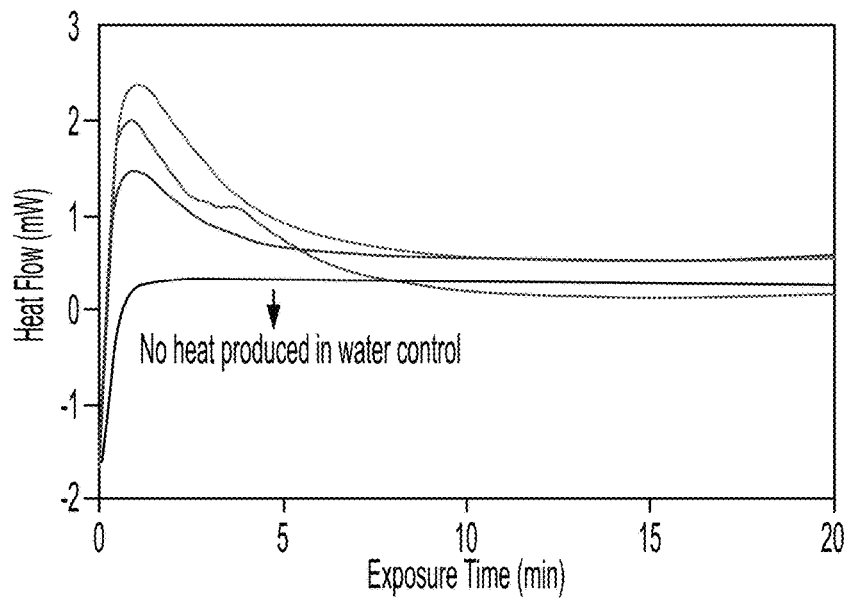
Fig. 2B
| | UV intensity (mW/cm²) | Solution (µL) | A (mg) | B (mg) | Ratio (B:A) | Enthalpy (J/g) |
|---|---|---|---|---|---|---|
| Black | 25 | 20 | 0 | 0 | 0 | 0 |
| Blue | 25 | 20 | 0.15 | 1.71 | 11:1 | 8.4 |
| Green | 25 | 20 | 0.29 | 3.42 | 11:1 | 17.6 |
| Red | 25 | 20 | 0.17 | 4.1 | 24:1 | 21.8 |
Fig. 2C

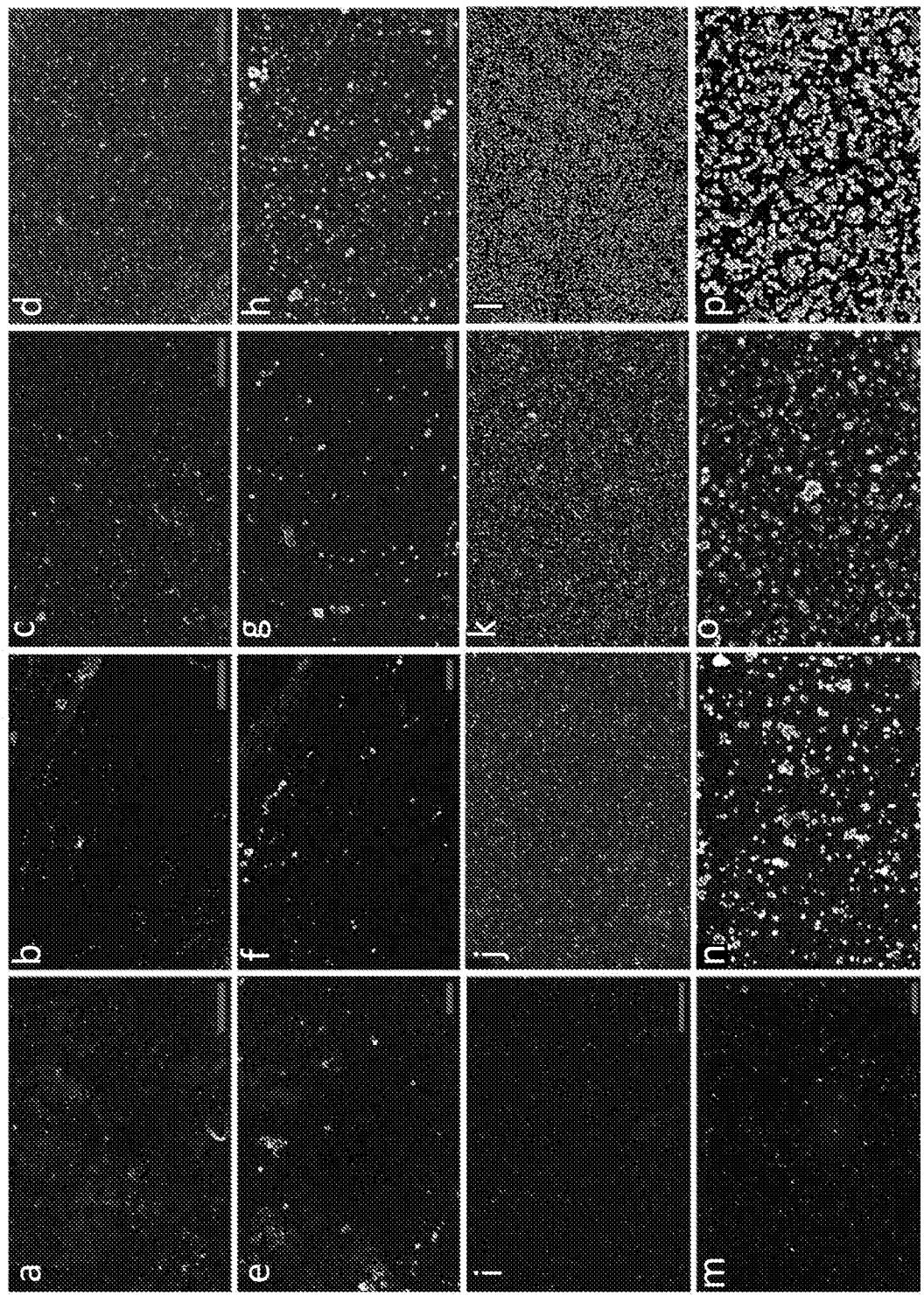
Fig. 3A-P

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Lys Leu Trp Val Leu Pro Lys Gly Gly Gly Cys
1               5                   10

COMPOSITIONS AND METHODS FOR INHIBITING POST-SURGICAL ADHESIONS

CROSS-REFERENCE TO RELATED APPLICATIONS

This application is a 35 U.S.C. § 371 national stage of International Application No. PCT/US2020/017021, filed Feb. 6, 2020, which claims the benefit of priority to U.S. Provisional Application No. 62/802,033 filed Feb. 6, 2019, which is are herein incorporated by reference in its their entirety for all purposes.

GOVERNMENT INTEREST

This invention was made with government support under grant numbers CA178748, CA150391, and CA198999 awarded by the National Institutes of Health. The government has certain rights in the invention.

REFERENCE TO A SEQUENCE LISTING SUBMITTED AS A TEXT FILE VIA EFS WEB

The Sequence Listing written in file 035052-542267_ST25.txt is 491 bytes, was created on Feb. 4, 2020, and is hereby incorporated by reference.

FIELD

The present invention relates to compositions and methods for inhibiting post-surgical adhesion formation and, in particular, to particle compositions forming composite membranes for inhibiting post-surgical adhesion formation.

BACKGROUND

Abdominal surgery is an important treatment in many diseases, such as cancers and inflammatory bowel diseases. A frequent side effect of abdominal surgery is the formation of peritoneal adhesions. It has been reported that up to 93% of patients who underwent abdominal surgery were found to have postsurgical adhesion. Such adhesions can cause pain, bowel obstruction as well as other serious complications. The biology of adhesion formation is highly complex, involving many chemical mediators, cytokines, and cell types. It is thought to be due to the imbalance between inflammatory and healing processes. Pro-inflammatory processes, such as macrophage activation and fibroblast activation, are known to play an important role in adhesion formation.

Current strategies to minimize adhesions mainly involve the use of anatomical barriers between injured peritoneal surfaces to prevent adhesion formation. Such barriers include adhesion-reducing liquids and polymer-based barriers (e.g. cellulose) that are in the form of gels or films. Adhesion-preventing liquids generally contain polymers such as icodextrin or polyethylene glycol (PEG). They function by occupying the abdominal cavity and allowing injured surfaces to heal undisturbed. Recent meta-analysis has shown that the use of adhesion barriers (both liquids and films/gels) in abdominal surgery likely reduce the formation of adhesions. However, the effects are moderate. Moreover, for several formulations, including icodextrin, PEG, and oxidized regenerated cellulose, there is no clear evidence that they can reduce the complications resulting from post-operative adhesions. The lack of efficacy from adhesion-preventing liquids is likely due to their absorption by the peritoneal cavity, thus not providing a persistent barrier on injured surfaces. Polymer films and gels have been used as barriers but these non-targeted and bulk barriers are not always able to cover all injured peritoneal surfaces. Moreover, these barriers do not always stay in place post-surgery, thus limiting their therapeutic efficacy.

SUMMARY

In view of these deficiencies, there has been strong interest in the development of strategies and agents that can prevent post-surgical adhesion formation.

In one aspect, methods are described herein employing particle compositions operable to form composite membranes for inhibition of post-surgical adhesions. For example, a method of treating a surgical site comprises contacting the surgical site with a particle formulation comprising targeting particles and scaffolding particles. The targeting particles and scaffolding particles are crosslinked to provide a composite membrane at the surgical site, wherein formation of post-surgical adhesions are inhibited by the composite membrane. As detailed further herein, the targeting particles and scaffolding particles can be crosslinked subsequent to application to the surgical site, thereby enabling formation of the composite membrane in vivo. In some embodiments, the surgical site comprises peritoneal surfaces.

In another aspect, the subject matter described herein is directed to a method of treating a surgical site comprising contacting the surgical site with a particle formulation comprising carrier particles and scaffolding particles.

In another aspect, the subject matter described herein is directed to a kit comprising:
  (i) a vial containing a first particle formulation comprising targeting particles; and
  (ii) a vial containing a second particle formulation comprising scaffolding particles.

In another aspect, the subject matter described herein is directed to a kit comprising:
  (i) a vial containing a first particle formulation comprising carrier particles; and
  (ii) a vial containing a second particle formulation comprising scaffolding particles.

In another aspect, the subject matter described herein is directed to a composition comprising targeting particles and scaffolding particles.

In another aspect, the subject matter described herein is directed to a composition comprising carrier particles and scaffolding particles.

In another aspect, the subject matter described herein is directed to a composite membrane formed by crosslinking a first particle composition comprising targeting particles with a second particle composition comprising scaffolding particles.

In another aspect, the subject matter described herein is directed to a composite membrane formed by crosslinking a first particle composition comprising carrier particles with a second particle composition comprising scaffolding particles.

In another aspect, the subject matter described herein is directed to a method of reducing peritoneal adhesions, wherein said peritoneal adhesions form subsequent to abdominal surgery, said method comprising:
  contacting an abdominal surgical site with targeting particles;
  contacting said targeting particles with scaffolding particles; and crosslinking the targeting particles and scaffolding particles to provide a composite membrane at the abdominal surgical site, wherein said peritoneal adhesions are reduced by said composite membrane.

In another aspect, the subject matter described herein is directed to a method of reducing peritoneal adhesions, wherein said peritoneal adhesions form subsequent to abdominal surgery, said method comprising:

contacting an abdominal surgical site with carrier particles;

contacting said carrier particles with scaffolding particles; and crosslinking the carrier particles and scaffolding particles to provide a composite membrane at the abdominal surgical site, wherein said peritoneal adhesions are reduced by said composite membrane.

These and other aspects are described herein.

BRIEF DESCRIPTION OF THE DRAWINGS

FIG. 1A shows the designs of the two nanoparticles that comprise the photo crosslinkable nano-patch (pCNP).

FIG. 2A shows pCNP formation from nanoparticles upon UV irradiation. Depicted is a reaction schematic for the photo-induced crosslinking of nanoparticles via the diazirine functional group of NP-B.

FIG. 2B shows a photo-DSC analysis of the crosslinking reaction with different NP-A and NP-B concentrations.

FIG. 2C shows the calculated reaction enthalpy during diazirine crosslinking.

FIG. 3A through FIG. 3P show how the pCNP forms a high-density nano-patch on collagen IV-enriched surface in vitro. FESEM images showing the formation of a nano-patch on non-coated (a-h) and collagen IV-coated (i-p) glass cover slides using different approaches. (a, e, i, m) NP-A without targeting ligand (NP-A'); (b, f, j, n) NP-A; (c, g, k, o) NP-B; (d, h, l, p) pCNP. a-d and i-l, FESEM images at 10,000 magnification. Scale bar=5 μm. e-h and m-p, FESEM images at 40,000 magnification. Scale bar=1 μm.

FIG. 7A shows representative photos showing PPE and the administration of pCNP. FIG. 7B shows representative photos demonstrating postsurgical adhesion in rats 14 days after different treatments: PBS, the injured area was incubated with saline for 10 min and another 10 min under UV irradiation; A only, the injured area was incubated with NP-A for 10 min, washed and incubated with saline for another 10 min under UV irradiation; A+A, the injured area was incubated with NP-A for 10 min, washed with saline twice, then incubated with NP-A again for another 10 min under UV irradiation; A'+B, the injured area was incubated with NP-A' (NP-A without targeting ligand) for 10 min, washed with saline twice, then incubated with NP-B for another 10 min under UV irradiation; pCNP w/o Dex, the injured area was incubated with NP-A without dexamethasone 21-palmitate for 10 min, washed with saline twice, then incubated with NP-B for another 10 min under UV irradiation; Seprafilm®, the injured area was incubated with saline for 10 min and another 10 min under UV irradiation, the saline was removed and the injured area was covered with Seprafilm®; pCNP, the injured area was incubated with NP-A for 10 min, washed with saline twice, then incubated with NP-B for another 10 min under UV irradiation. (FIG. 7C-FIG. 7J) FIG. 7C depicts representative H&E staining histology tissue images showing the thickness of adhesion/fibrosis in untreated rats, and rats that underwent surgery and subsequent treatment with PBS (FIG. 7D), NP-A only (FIG. 7E), NP-A+NP-A (FIG. 7F), NP-A'+NP-B (FIG. 7G), pCNP without dexamethasone 21-palmitate (FIG. 7H), Seprafilm® (FIG. 7I) and pCNP (FIG. 7J). Scale bar=2 mm. (FIG. 7K and FIG. 7L) Qualitative (FIG. 7K) and quantitative (FIG. 7L) scoring analysis of postsurgical adhesion on rats 14 days after treatments. Statistical significance was assessed using Mann Whitney test. Data represents scatter dot plot with median line (For A+A, n=6; For pCNP w/o Dex, n=7; For Seprafilm®, n=8; For other groups, n=9). *P<0.05, P<0.01, *P<0.001, ****P<0.0001. (FIG. 7M) Quantitative assessment of the adhesion/fibrosis thickness in (d)-(j). Statistical significance was assessed using unpaired two-tailed t-test. Data represents mean±standard error of the mean (SEM) (n=3). *P<0.05, P<0.01, *P<0.001, ****P<0.0001.

(FIG. 15A-FIG. 15C) Blood test at 6 h, 24 h, 48 h and 72 h after treatments: red blood cell count (FIG. 15A), white blood cell count (FIG. 15B), blood glucose concentration (FIG. 15C). Data represents mean±standard error of the mean (SEM) (For A+A, n=6; For pCNP w/o Dex, n=7; For Seprafilm®, n=8; For other groups, n=9).

FIG. 20A depicts FESEM images showing the retention and biodegradation of pCNP on rats' abdominal wall at 6 h, 24 h, 72 h, 1 week and 2 weeks after surgery and subsequent treatment with pCNP. Scale bar=200 nm. Hematoxylin and eosin (H&E) staining images (FIG. 20B) and CD45 immunohistochemistry (IHC) staining images (FIG. 20C) showing the local inflammation on rats' abdominal wall at 6 h, 24 h, 72 h, 1 week and 2 weeks after surgery and subsequent treatment with pCNP. For (FIG. 20B), scale bar=500 µm; For (FIG. 20C), scale bar=100 µm.

DETAILED DESCRIPTION

Figure 1B:
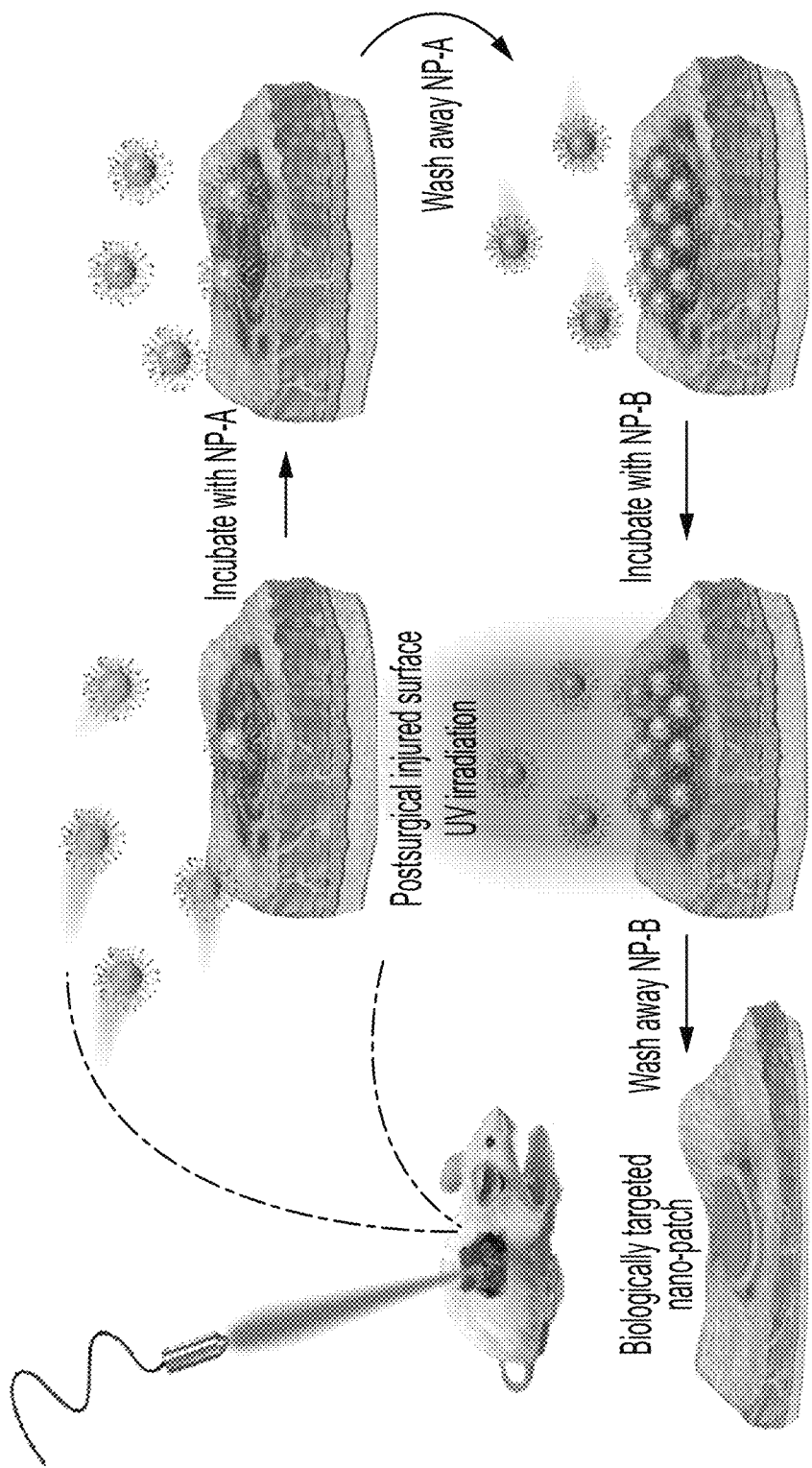
FIG. 1B shows a schematic of the formation of pCNP on an injured surface to prevent postsurgical peritoneal adhesion.

Postsurgical adhesion is a common complication from surgical treatment. Despite its prevalence, there has been limited advance in its treatment. This is largely due to the difficulty of providing barriers over all injured epithelial/mesothelial surfaces. In addition, medical therapies such as anti-inflammatories have systemic side effects that limit their use. Described herein is a novel biologically targeted barrier system (photo-crosslinkable nano-patch, pCNP) that can also incorporate medical therapies to prevent postsurgical adhesions.

To achieve targeting, peptides are used that bind to collagen as targeting ligands. Since collagen/basement membranes are exposed when epithelium/mesothelium is injured, the collagen targeted nanoparticles will bind to areas of tissue injury (denuded epithelium and mesothelium). Using in vitro and in vivo studies, the biological targeting is demonstrated as being highly specific. In certain embodiments, dexamethasone is also incorporated into the system to reduce inflammation and promote normal healing. As seen in the in vivo studies, the addition of dexamethasone is successful in further reducing adhesion formation.

It is demonstrated using a rat PPE model that the pCNP can effectively prevent surgical adhesions in vivo, better than the commercial adhesion barrier SEPRAFILM. Moreover, the pCNP did not show any significant toxicity. pCNP can improve quality of life of surgical patients as well as reduce surgical complications due to peritoneal adhesion.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used herein, "PPE" refers to parietal peritoneum excision.

As used herein, "surgical site" or "abdominal surgical site" refers to tissues around a surgical incision, organs adjacent to the incision, and generally surfaces in the peritoneal cavity. For example, compositions and methods described herein can be applied to injured peritoneal surfaces following abdominal surgery.

As used herein, "peritoneal adhesions" refer to a condition in which pathological bonds form between the omentum, the small and large bowels, the abdominal wall, and other intra-abdominal organs.

As used herein, "post-surgical adhesions" refers to adhesions that develop following surgery. In particular, abdominal adhesions are bands of fibrous scar tissue that form on organs in the abdomen. They can cause organs to stick to one another or to the wall of the abdomen.

As used herein, "reducing peritoneal adhesions" refers to the reduction of post-surgical adhesions by about 10%, 20%, 25%, 30%, 35%, 40%, 45%, 50%, 55%, 60%, 65%, 75%, 80%, 85%, 90%, 95%, 96%, 97%, 98%, or 99% through application of the composite membranes described herein, compared to methods that do not use the composite membranes.

As used herein, "inhibition of post-surgical adhesions" by the composite membrane refers to the reduction of post-surgical adhesions by about 10%, 20%, 25%, 30%, 35%, 40%, 45%, 50%, 55%, 60%, 65%, 75%, 80%, 85%, 90%, 95%, 96%, 97%, 98%, or 99% compared to methods without the composite membrane.

As used herein, "subsequent to abdominal surgery" refers to a time period (i.e. 1 hr, 2 hr, 10 hr, 24 hr, 48 hr, 36 hr, 54 hr, 72 hr, 100 hr, 5 days, 7 days, 10 days, 12 days, 14 days, 20 days, 30 days, 40 days, 50 days, 60 days) after which a subject undergoes abdominal surgery.

Unless otherwise specified, the terms "composition" and "formulation" as used herein are intended to encompass a product comprising the specified ingredient(s) (and in the specified amount(s), if indicated), as well as any product which results, directly or indirectly, from combination of the specified ingredient(s) in the specified amount(s). Additionally, the terms "composition" and "formulation" refer to a mixture of compounds or particles.

Additional definitions are provided below.

II. Particle Compositions and Composite Membranes

In embodiments, the subject matter described herein is directed to a composition comprising targeting particles and scaffolding particles.

As used herein, targeting particles refer to particles that comprise one or more chemical moieties targeting one or a variety of biomolecular species located at the site of peritoneal injury. The site of peritoneal injury includes tissues around a surgical incision, organs adjacent to the incision, and generally surfaces in the peritoneal cavity. Non-limiting examples of biomolecular species are collagen IV, laminin, entactin, integrin, fibronectin, vitronectin, proteoglycans, BM-40/osteonectin/SPARC, BM-90, bFGF. Examples of proteoglycans include heparin sulfate, perlecan, and agrin. Generally, cells and/or tissue targeted by the targeting particle include a target, which is specifically bound by the targeting moiety of the particle. Particle surfaces, for example, can be modified with targeting ligands of any desired functionality. In some embodiments, targeting ligands and/or other targeting moieties can bind the targeting particles to surfaces of the surgical site, such peritoneal surfaces. Targeting moieties, for example, can comprise a carbohydrate, a fatty acid, a glycopeptide, a glycoprotein, a lipid, a peptide, a polymer, a polynucleotide, a protein, or a small molecule. In some embodiments, the targeting moiety is a folic acid analogue, an antibody or an antibody fragment, or an aptamer. In a preferred embodiment, the targeting moiety is a collagen IV-targeting peptide. In certain embodiments, the collagen IV-targeting peptide has an amino acid sequence of KLWVLPKGGGC (SEQ ID NO: 1). In certain embodiments, the sequence exhibits 80% homology, 90% homology, 95% homology, or 99% homology.

Moreover, the targeting particles can further comprise at least one pharmaceutical composition for release at the surgical site. Pharmaceutical compositions carried or transported by the targeting particles can disrupt or inhibit one or more mechanisms or pathways of post-surgical adhesion formation. The pharmaceutical composition, for example, can inhibit tissue inflammation by reducing the presence of inflammatory cytokines and/or chemokines at the surgical site. The pharmaceutical composition, in some embodiments, comprises dexamethasone palmitate or related compound(s). A related compound is dexamethasone. Targeting particles can have any desired loading of a pharmaceutical composition. Pharmaceutical composition loading of a targeting particle can be determined according to several considerations including, but not limited to, particle construction, particle size, chemical identity of the pharmaceutical, and/or desired dosage amount. In some embodiments, targeting particles comprise a pharmaceutical loading of 10 μg/mg to 500 μg/mg. In other embodiments, targeting particles comprise a pharmaceutical loading of about 15 μg/mg, 20 μg/mg, 25 μg/mg, 30 μg/mg, 35 μg/mg, 40 μg/mg, 45 μg/mg, 50 μg/mg, 55 μg/mg, 60 μg/mg, 65 μg/mg, 70 μg/mg, 75 μg/mg, 80 μg/mg, 85 μg/mg, 90 μg/mg, 95 μg/mg, 100 μg/mg, 150 μg/mg, 200 μg/mg, 250 μg/mg, 300 μg/mg, 350 μg/mg, 400 μg/mg, or 450 μg/mg. In a preferred embodiment, targeting particles comprise a pharmaceutical loading of about 65.2 μg/mg.

In certain embodiments, the entire targeting particle is biodegradable. In other embodiments, only a portion of the targeting particle is biodegradable (e.g., the outer layer of the particle). In general, a biodegradable substance is one that can be broken down under physiological conditions. In some embodiments, one or more components of the targeting particles are biocompatible. Targeting particles can be solid or hollow. Targeting particles can comprise one or more layers (e.g., nanoshells, nanorings). In some embodiments, the targeting particles can be coated. In certain embodiments, the particles include an outer lipid monolayer. In other embodiments, the particles include an outer lipid bilayer. In further embodiments, the targeting particles include a polymeric outer layer.

Targeting particles can be formed of one or more polymeric materials, in some embodiments. In some embodiments, the pharmaceutical composition and/or targeting moiety can be associated with the surface of, encapsulated within, surrounded by, and/or dispersed throughout a polymeric matrix. A targeting particle, for example, can include a polymeric core. In certain embodiments, polymer used in the particle may comprise a natural or a semisynthetic polymer. Non-limiting examples of such polymers include albumins, aliginic acids, carboxymethylcelluloses, sodium sale cross-linked, celluloses, cellulose acetates, cellulose acetate butyrates, cellulose acetate phthalates, cellulose acetate trimelliates, chitins, chitos, collagens, dextrins, ethylcelluloses, gelatins, poloxamers, polysaccharides, sodium starch glycolates, starch thermally modified, tragacanth gums, or xanthangums polysaccharides.

In other embodiments, polymer of a targeting particle may be a synthetic polymer. Non-limiting examples of synthetic polymers include cellophane (polyethylene-coated), monomethoxypolyethylene glycols (mPEG), nylons, polyacetals, polyacrylates, poly(alkylene oxides), polyamides, polyamines, polyanhydrides, polyargines, polybutylene oxides (PBO), polybutyolactones, polycaprolactones (PCL), polycarbonates, polycyanoacrylates, poly(dioxanones) (PDO), polyesters, polyethers, polyethylenes, poly(ethylene-propylene) copolymers, poly(ethylene glycols) (PEG), poly(ethyleneimines), polyethylene oxides (PEO), polyglycolides (PGA), polyhydroxyacids, polylactides (PLA), polylysines, polymethacrylates (PMA), poly(methyl vinyl ethers) (PMV), poly(N-vinylpyrrolidines) (NVP), polyornithines, poly(orthoesters) (POE), polyphosphazenes, polypropiolactones, polypropylenes, polypropylene glycols) (PPG), polypropylene oxides (PPO), polypropylfumerates, polyserines, polystyrenes, polyureas, polyurethanes, polyvinyl alcohols (PVA), poly(vinyl chlorides)(PVC), poly (vinyl pyrrolidines) or silicon rubbers).

Polymer of a targeting particle may be a homopolymer, copolymer, or block copolymer comprising monomers from one or more the polymers above. If the polymer comprises asymmetric monomers, it may be regio-regular, isotactic or syndiotactic (alternating); or region-random, atactic. If the polymer comprises chiral monomers, the polymer may be stereo-regular or a racemic mixture, e.g. poly(D-, L-lactic acid). It may be a random copolymer, an alternating copolymer, a periodic copolymer, e.g., repeating units with a formula such as $[A_nB_m]$. The polymer may be a linear polymer, a ring polymer, a branched polymer, e.g., a dendrimer. The polymer may or may not be cross-linked. The polymer may be a block copolymer comprising a hydrophilic block polymer and a hydrophobic block polymer.

The polymer may comprise derivatives of individual monomers chemically modified with substituents, including without limitation, alkylation, e.g., (poly $C_1$-$C_{16}$ alkyl methacrylate), amidation, esterification, either, or salt formation. The polymer may also be modified by specific covalent attachments the backbone (main chain modification) or ends of the polymer (end group modifications). Examples of such modifications include attaching PEG (PEGylation) or albumin.

In certain embodiments, polymer of a targeting particle may be a poly(dioxanone), such as poly(p-dioxanone), see U.S. Pat. Nos. 4,052,988; 4,643,191; 5,080,664; and 5,019,094, the contents of which are hereby incorporated by reference in their entirety. The polymer may be a copolymer of poly(alkylene oxide) and poly(p-dioxanone), such as a block copolymer of poly(ethylene glycol) (PEG) and poly (p-dioxanone) which may or may not include PLA, see U.S. Pat. No. 6,599,519, the content of which is hereby incorporated by reference in its entirety. In a preferred embodiment, the targeting particle is a poly(ethylene glycol)-poly(lactic-co-glycolic acid) block copolymer (PEG-PLGA).

Polymer of a targeting particle can be a polyester, a polyester-polycation copolymer, a polyester-polysugar copolymer, see U.S. Pat. No. 6,410,057, the content of which is hereby incorporated by reference in its entirety.

In some embodiments, targeting particles employ a polymeric matrix, such as a polyethylene oxide (POE) matrix. Examples of POE block copolymers include U.S. Pat. Nos. 5,612,052 and 5,702,717, the contents of which are hereby incorporated by reference in their entirety. In some embodiments, a polymeric matrix may be a polylactide (PLA), including poly(L-lactic acid), poly (D-lactic acid), poly(D-, L-lactic acid); a polyglycolide PGA; poly(lactic-co-glycolic acid) (PLGA); poly (lactic-co-dioxanone) (PLDO) which may or may not include polyethylene glycol (PEG). See U.S. Pat. Nos. 4,862,168; 4,452,973; 4,716,203; 4,942,035; 5,384,333; 5,449,513; 5,476,909; 5,510,103; 5,543,158; 5,548,035; 5,683,7230 5,702,717, 6,616,941 (e.g., Table 1); 6,916,788 (e.g., Table 4, PLA-PEG, PLDO-PEG, PLGA-PEG), 7,217,770 (PEG-PLA); U.S. Pat. No. 7,311,901 (amphophilic copolymers); U.S. Pat. No. 7,550,157 (mPEG-PCL, mPEG-PLA, mPEG-PLDO, mPEG-PLGA, and micelles); U.S. Pat. Pub. No. 2010/0008998 (Table 2, PEG2000/4000/10,000-mPEG-PLA); PCT Pub. Nos. 2009/084801 (mPEG-PLA and mPEG-PLGA micelles), the contents of which are hereby incorporated by reference in their entirety. In some embodiments, a polymeric matrix can comprise proteins, lipids, surfactants, carbohydrates, small molecules, and/or polynucleotides. In some embodiments, a targeting particle comprises a polymeric core coated with lipid (e.g., a lipid monolayer or lipid bilayer). In certain embodiments, the particle is a liposome or a micelle. Pharmaceutical composition and/or targeting agent to be delivered may be inside the particle (e.g., in the core), in the shell or coating portion of the particle, or associated with the surface of the particle.

In further embodiments, targeting particles can be non-polymeric particles (e.g., metal particles, quantum dots, ceramics, inorganic materials, bone, etc.). Non-limiting examples of non-polymeric materials for the targeting particles include a material selected from the group consisting of alumina ($Al_2O_3$), titania ($TiO_2$), zirconium oxide ($ZrO_2$), silicon carbide (SiC), silicon dioxide ($SiO_2$), spinel ($MgAl_2O_4$), mullite selected from $3Al_2O_3$-$2SiO_2$ or $2Al_2O_3$—$SiO_2$, aluminum nitride (AlN), aluminum carbide ($Al_4C_3$), silicon nitride ($Si_3N_4$), silicon carbon nitride (SiCN), silicon aluminum carbon nitride (SiAlCN), zinc oxide (ZnO), Barium titanate ($BaTiO_3$), boron oxide, boron nitride, zirconium nitride (ZrN), titanium carbide (TiC), titanium nitride (TiN), Pd, Ag, Cu, Fe, Ni, W, Ti, Mo, Zn, Pt, Sn, Pb, Ga, Mg, Bi, Al, stainless steel, carbon nanotubes (CNTs), carbon nanofibers (CNFs), graphene, carbon nanohorns (CNHs), carbon fiber, and carbon nanoparticles (CNPs). In some embodiments, the pharmaceutical composition to be delivered and/or targeting moiety can be covalently associated with a non-polymeric particle. In some embodiments, the pharmaceutical compositions to be delivered and/or targeting moiety is non-covalently associated with a non-polymeric particle.

Targeting particles can have any size consistent with the objectives of the present invention. Targeting particles, for example, can be nanoparticles, microparticles or mixtures thereof. In some embodiments, a targeting particle measures less than 500 µm or less than 300 µm in at least one dimension (e.g., diameter or length). Targeting particles may also measure less than 100 µm, less than 75 µm, less than 50 µm, or less than 10 µm in at least one dimension. In some embodiments, targeting particles measure less than 1000 nanometers (nm) in at least one dimension. Targeting nanoparticles, for example, can measure less than 900 nm, 800 nm, 700 nm, 600 nm, 500 nm, 400 nm, 300 nm, 200 nm, or 100 nm in a least one dimension. In further embodiments, a targeting nanoparticle is about 50 nm to about 200 nm in at least one dimension. In certain embodiments, the targeting particles are about 125 nm, 130 nm, 135 nm, 140 nm, 145 nm, 150 nm, 155 nm, 160 nm, 161 nm, 162 nm, 163 nm, 164 nm, 165 nm, 166 nm, 167 nm, 168 nm, 169 nm, or 170 nm in diameter. In a preferred embodiment, the targeting particles are about 166 nm in diameter.

In embodiments, the targeting particles carry a charge. In certain embodiments, the targeting particles have a negative surface charge of about −3 to about −25 mV. In certain embodiments, the targeting particles have a surface charge of about −8 mV, −9 mV, −10 mV, −11 mV, −12 mV, −13 mV, −14 mV, −15 mV, −16 mV, or −17 mV. In a preferred embodiment, the targeting particles have a negative surface charge of about −12 mV.

The scaffolding particles can have any architecture consistent with the objectives of the present invention. In some embodiments, the scaffolding particles exhibit a polymeric core/shell architecture. As used herein, the term "core-shell structure" refers to a composite particle comprising at least two different components, where one component is located at the center as a core and the second component surrounds the core as a shell. Non-limiting examples of core-shell structure polymer types include metal-core and different metal shell, metal-core and nonmetal shell, metal-core and polymer shell, nonmetal-core and nonmetal shell, polymer-core and nonmetal shell, and polymer-core and polymer shell where the two polymers are different. The scaffolding particles can be employed to impart various properties to the composite membrane including, but not limited to, increased density and desirable mechanical properties and/or rheological properties such as elastic modulus, tensile strength and compressive strength. In some embodiments, the scaffolding particles are non-hydrogel particles. As used herein, hydrogel particles refer to a network of polymer chains that are hydrophilic and which are sometimes found as a colloidal gel in which water is the dispersion medium. Scaffolding particles can be formed of any material and can have any size recited hereinabove for the targeting particles. In certain embodiments, the scaffolding particles are about 130 nm, 135 nm, 140 nm, 145 nm, 150 nm, 155 nm, 160 nm, 165 nm, 170 nm, 171 nm, 172 nm, 173 nm, 174 nm, 175 nm, 176 nm, 177 nm, 178 nm, 179 nm, or 180 nm in diameter. In a preferred embodiment, the scaffolding particles are about 175 nm in diameter.

Size of the targeting particles can be selected independent of scaffolding particle size. Alternatively, sizes of the targeting particles and the scaffolding particles can be selected in conjunction with one another. Additionally, the targeting particles and scaffolding particles can have any desired shape or morphology. The targeting particles and scaffolding particles may independently exhibit a spherical shape, elliptical shape, polygonal shape or irregular shape. Shapes and sizes of the particles can be selected to promote particle packing characteristics for enhancing one or more properties of the composite membrane. In a preferred embodiment, the particles have a spherical morphology.

The targeting particles and scaffolding particles, in some embodiments, interact with one another via ionic or electrostatic interactions prior to crosslinking. For example, the targeting particles and scaffolding particles can interact via attractive dipole-dipole forces. Alternatively, the targeting particles and scaffolding particles may also exhibit oppositely charged surfaces for promoting ionic binding between the particles.

In embodiments, the scaffolding particles carry a charge. In certain embodiments, the scaffolding particles have a positive surface charge of about 3 to about 50 mV. In certain embodiments, the scaffolding particles have a positive surface charge of about 17 mV, 18 mV, 19 mV, 20 mV, 21 mV, 22 mV, 23 mV, 24 mV, 25 mV, 26 mV, 27 mV, 28 mV, 29 mV, or 30 mV. In a preferred embodiment, the scaffolding particles have a positive surface charge of about 23 mV.

The surgical site is contacted with the particle formulation comprising the targeting and scaffolding particles. In some embodiments, targeting particles and scaffolding particles are independently applied to the surgical site. For example, the targeting particles can be applied to the surgical site prior to application of the scaffolding particles. Alternatively, the scaffolding particles are applied to the surgical site prior to application of the targeting particles. In further embodiments, the targeting and scaffolding particles are simultaneously applied to the surgical site.

As described herein, the targeting particles and scaffolding particles are crosslinked to provide a composite membrane at the surgical site, wherein formation of post-surgical adhesions are inhibited by the composite membrane. Specific crosslinking mechanisms can be dependent on the specific architectures of the targeting particles and scaffolding particles. The crosslinking, for example, can be photo-initiated. In a preferred embodiment, photo-initiation proceeds with UV light. In certain embodiments, the wavelength of light is between 250 and 450 nm. In certain embodiments, the wavelength of UV light is about 300 nm, 325 nm, 330 nm, 335 nm, 340 nm, 345 nm, 350 nm, 355 nm, 360 nm, 361 nm, 362 nm, 363 nm, 364 nm, 365 nm, 366 nm, 367 nm, 368 nm, 369 nm, or 370 nm. In a preferred embodiment, the crosslinking is photo-initiated with UV light having a wavelength of about 365 nm. In some embodiments, the scaffolding particles or targeting particles comprise a photolabile group to effectuate the crosslinking. In a preferred embodiment, the scaffolding particles comprise a photolabile group to effectuate the crosslinking. In certain embodiments, the photolabile group is a diazirine group. In other embodiments, photoinitiator separate from the scaffolding particles and targeting particles can be employed in the crosslinking process. The photoinitiator can be part of the particle formulation or independently added to the surgical site. In further embodiments, non-photo-initiated crosslinking systems may be employed, such as isocyanate crosslinking mechanisms. Table I provides a listing of various systems that may be employed in some embodiments of particle crosslinking described herein. FIG. 24 depicts several of these systems.

TABLE I

| Crosslinking Systems | |
|---|---|
| Photo-initiated Systems | Non-photo-initiated Systems |
| diazirine reaction between carbene and C-WN-HIO-H under UV | carbodiimide chemistry between amine and carboxyl/NHS ester/imidoester/pentafluorophenyl ester/hydroxymethyl phosphine |
| aryl azide reaction between aryl azide and double bond/C-H/N-H/primary amine under UV | sulfhydryl reaction between thiol and maleimide/haloacetyl/pyridyldisulfide/thiosulfonate/vinylsulfone |
| thiol-ene chemistry between thiol and alkene under UV | aldehyde reaction between aldehyde and hydrazide/alkoxyamine |
| methacrylate polymerization under UV | hydroxyl reaction between hydroxyl and isocyanate |
| | click chemistry between azide and alkyne/DBCO(Dibenzocyclooctyne)/TCO (Tetrazine-trans-Cyclooctene)/etc., or tetrazien and alkene |
| | avidin-biotin interaction between biotin and avidin/streptavidin/neutravidin |

Pharmaceutical compositions of the targeting particles can be released from the composite membrane. As detailed above, the pharmaceutical composition can assist in inhibiting formation of post-surgical adhesions. Release rates of the pharmaceutical composition from the composite membrane can be dependent on several considerations including, but not limited to, identity of the pharmaceutical composition, compositional identity of the targeting particles and/or scaffolding particles and macroscopic properties of the composite membrane, such as thickness, density and porosity. In some embodiments, greater than 10 percent of a pharmaceutical composition is released within 24 hours of membrane formation. In certain embodiments, about 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, or 70% of one or more of the pharmaceutical compositions are released within 24 hours of membrane formation. In a preferred embodiment, about 13.5% or 19.1% of the one or more pharmaceutical compositions are released within 24 hours of membrane formation. In a further preferred embodiment, about 13.5% Dex-Pal and about 19.1% Dex are released within 24 hours of membrane formation. Moreover, the composite membrane can exhibit sustained release of pharmaceutical compositions. One or more pharmaceutical compositions can be released over a time period of at least 14 days, for example. In certain embodiments, the one or more pharmaceutical compositions are released over a time period of at least 15, 16, 17, 18, 19, 20, 21, 22, 23, 24, 25, 26, 27, 28, 29, 30, 35, 40, 45, or 50 days. In some embodiments, the scaffolding particles may contain one or more pharmaceutical compositions. Pharmaceutical compositions carried by the scaffolding particles may be different than the pharmaceutical composition(s) carried by the targeting particles.

In another aspect, a method of treating a surgical site comprises contacting the surgical site with a particle formulation comprising scaffolding particles and carrier particles. In certain embodiments, the subject matter described herein is directed to a composition comprising carrier particles and scaffolding particles. As used herein, "carrier particles" refer to particles that transport one or more pharmaceutical compositions to the surgical site. The scaffolding particles and carrier particles are crosslinked to provide a composite membrane at the surgical site, wherein formation of post-surgical adhesions are inhibited by the composite membrane. The pharmaceutical composition can comprise any pharmaceutical composition described herein, including compositions that inhibit tissue inflammation. Similarly, the carrier particles, scaffolding particles and composite membrane can have any composition and/or properties described hereinabove.

In certain embodiments, the subject matter described herein is directed to a composite membrane formed by crosslinking a first particle composition comprising targeting particles with a second particle composition comprising scaffolding particles.

In certain embodiments, the subject matter described herein is directed to a composite membrane formed by crosslinking a first particle composition comprising carrier particles with a second particle composition comprising scaffolding particles.

As used herein, "composite membrane" refers to the material produced by the crosslinking of the individual targeting particles or carrier particles and scaffolding particles. In certain embodiments, when the composite membrane is produced by a formulation comprising nanoparticles, the composite membrane can be referred to as a "nano-patch."

III. Articles of Manufacture

In another aspect, described herein are articles of manufacture, for example, a "kit" containing materials useful for preventing post-surgical adhesions. In certain embodiments, the kit comprises (i) a vial containing a first particle formulation comprising targeting particles; and (ii) a vial containing a second particle formulation comprising scaffolding particles. In other embodiments, the kit comprises (i) a vial containing a first particle formulation comprising carrier particles; and (ii) a vial containing a second particle formulation comprising scaffolding particles. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister packs, etc. The container may be formed from a variety of materials such as glass or plastic. The label or package insert indicates that the particles are useful for preventing post-surgical adhesions. Alternatively, or additionally, the article of manufacture may further comprise a second container comprising phosphate-buffered saline, Ringer's solution, or dextrose solution. It may further include other materials desirable from a commercial and user standpoint, including diluents, filters, needles, and syringes.

The kit may further comprise directions for the administration of the particles. For example, since the kit comprises a vial containing a first particle formulation comprising targeting particles or carrier particles, and a vial containing a second particle formulation comprising scaffolding particles, the kit may further comprise directions for the simultaneous, sequential, or separate administration of the targeting or carrier particles and the scaffolding particles. The kit may additionally comprise instructions for how to crosslink the particular particles.

In certain embodiments, the kit can comprise a material, chemical, or device to promote crosslinking of the two particles to form a composite membrane.

In certain other embodiments the individual components of the kit may comprise a container for containing the separate compositions such as a divided bottle or a divided foil packet, however, the separate compositions may also be contained within a single, undivided container. Typically, the kit comprises directions for the use of the separate components.

IV. Methods

In certain embodiments, the subject matter described herein is directed to a method of treating a surgical site comprising:
  contacting the surgical site with a particle formulation comprising targeting particles and scaffolding particles; and
  crosslinking the targeting particles and scaffolding particles to provide a composite membrane at the surgical site, wherein formation of post-surgical adhesions are inhibited by the composite membrane.

In certain embodiments, the subject matter described herein is directed to a method of reducing peritoneal adhesions, wherein said peritoneal adhesions form subsequent to abdominal surgery, said method comprising:
  contacting an abdominal surgical site with targeting particles;
  contacting said targeting particles with scaffolding particles; and
  crosslinking the targeting particles and scaffolding particles to provide a composite membrane at the abdominal surgical site, wherein said peritoneal adhesions are reduced by said composite membrane.

In certain embodiments of the above methods, after contacting said targeting particles with said surgical site, said targeting particles are contacted with a saline solution.

In certain embodiments of the above methods, the targeting particles comprise one or more chemical moieties targeting one or more biomolecular species located at the surgical site.

In certain embodiments of the above methods, the one or more biomolecular species is selected from the group consisting of collagen IV, laminin, entactin, integrin, fibronectin, vitronectin, proteoglycans, BM-40/osteonectin/SPARC, BM-90, and bFGF.

In a preferred embodiment of the above methods, the one of more biomolecular species is collagen IV.

In certain embodiments of the above methods, the one or more chemical moieties targeting one or more biomolecular species is a collagen IV-targeting peptide with an amino acid sequence of KLWVLPKGGGC (SEQ ID NO: 1).

In certain embodiments of the above methods, the targeting particles and/or scaffolding particles are nanoparticles, microparticles or mixtures thereof.

In certain embodiments of the above methods, the targeting particles and/or scaffolding particles are nanoparticles.

In certain embodiments of the above methods, the targeting particles comprise a polymeric structure.

In certain embodiments of the above methods, the targeting particles comprise a poly(ethylene glycol)-poly(lactic-co-glycolic acid) block polymer.

In certain embodiments of the above methods, the targeting particles further comprise one or more pharmaceutical compositions.

In certain embodiments of the above methods, the one or more pharmaceutical compositions inhibit tissue inflammation.

In certain embodiments of the above methods, the presence of inflammatory cytokines and/or chemokines at the surgical site is reduced.

In certain embodiments of the above methods, the method further comprises releasing the one or more pharmaceutical compositions from the composite membrane.

In certain embodiments of the above methods, greater than 10 percent of the one or more pharmaceutical compositions are released within 24 hours of membrane formation.

In certain embodiments of the above methods, the one or more pharmaceutical compositions is released over a time period of at least 14 days.

In certain embodiments of the above methods, the one or more pharmaceutical compositions is dexamethasone or dexamethasone palmitate.

In certain embodiments of the above methods, the scaffolding particles are non-hydrogel particles.

In certain embodiments of the above methods, the scaffolding particles comprise a core-shell architecture.

In a preferred embodiment, the scaffolding particles comprise a poly(lactic-co-glycolic acid) core and a polyethyleneimine shell.

In certain embodiments of the above methods, the targeting particles and scaffolding particles interact with one another via ionic or electrostatic interactions prior to crosslinking.

In certain embodiment of the above methods, the targeting particles and scaffolding particles are oppositely charged.

In certain embodiments, the targeting particles have a negative charge and the scaffolding particles have a positive charge.

In certain embodiments of the above methods, the crosslinking is photo-initiated.

In certain embodiments of the above methods, the photo-initiated crosslinking comprises the application of UV light.

In certain embodiments of the above method, the UV light has a wavelength of about 365 nm.

In certain embodiments of the above methods, the scaffolding particles comprise one or more photolabile groups.

In certain embodiments of the above methods, the one or more photolabile groups is a diazirine functional group.

In certain embodiments of the above methods, the composite membrane is biodegradable.

In certain embodiments of the above methods, the surgical site comprises peritoneal surfaces.

In certain embodiments of the above methods, the targeting particles are applied to the surgical site prior to application of the scaffolding particles to the surgical site.

In certain embodiments of the above methods, the targeting particles are bound to one or more surfaces of the surgical site. As used herein, "bound to one or more surfaces" refers to the targeting particle being localized to the surface, wherein the particle is resting, sitting, or adjacent to the surface.

In certain embodiments, the subject matter described herein is directed to a method of method of treating a surgical site comprising:
  contacting the surgical site with a particle formulation comprising scaffolding particles and carrier particles transporting one or more pharmaceutical compositions; and
  crosslinking the carrier particles and scaffolding particles to provide a composite membrane at the surgical site, wherein formation of post-surgical adhesions are inhibited by the composite membrane.

In certain embodiments, the subject matter described herein is directed to a method of reducing peritoneal adhesions, wherein said peritoneal adhesions form subsequent to abdominal surgery, said method comprising:
  contacting an abdominal surgical site with carrier particles;
  contacting said carrier particles with scaffolding particles; and
  crosslinking the carrier particles and scaffolding particles to provide a composite membrane at the abdominal surgical site, wherein said peritoneal adhesions are reduced by said composite membrane.

In certain embodiments of the above methods, after contacting said carrier particles with said surgical site, said carrier particles are contacted with a saline solution.

In certain embodiments of the above methods, one or more pharmaceutical compositions inhibit tissue inflammation.

In certain embodiments of the above methods, the presence of inflammatory cytokines and/or chemokines at the surgical site are reduced.

In certain embodiments of the above methods, the method further comprises releasing the one or more pharmaceutical compositions from the composite membrane.

In certain embodiments of the above methods, the one or more pharmaceutical compositions are released over a time period of at least 14 days.

In certain embodiments of the above methods, the one or more pharmaceutical compositions is dexamethasone or dexamethasone palmitate.

In certain embodiments of the above methods, the scaffolding particles are non-hydrogel particles.

In certain embodiments of the above methods, the scaffolding particles and/or carrier particles are nanoparticles, microparticles or mixtures thereof.

In certain embodiments of the above methods, the scaffolding particles and/or carrier particles are nanoparticles.

In certain embodiments of the above methods, the carrier particles comprise a poly(ethylene glycol)-poly(lactic-co-glycolic acid) block polymer.

In certain embodiments of the above methods, the scaffolding particles comprise a core-shell architecture.

In a preferred embodiment, the scaffolding particles comprise a poly(lactic-co-glycolic acid) core and a polyethyleneimine shell.

In certain embodiments of the above methods, the carrier particles and scaffolding particles interact with one another via ionic or electrostatic interactions prior to crosslinking.

In certain embodiments of the above methods, the carrier particles and scaffolding particles are oppositely charged.

In certain embodiments, the targeting particles have a negative charge and the scaffolding particles have a positive charge.

In certain embodiments of the above methods, the crosslinking is photo-initiated.

In certain embodiments of the above methods, wherein the photo-initiated crosslinking comprises the application of UV light.

In certain embodiments of the above method, the UV light has a wavelength of about 365 nm.

In certain embodiments of the above methods, the scaffolding particles comprise one or more photolabile groups.

In certain embodiments of the above methods, the one or more photolabile groups is a diazirine functional group.

In certain embodiments of the above methods, the composite membrane is biodegradable.

In certain embodiments of the above methods, the carrier particles comprise one or more chemical moieties targeting one or more biomolecular species located at the surgical site.

In certain embodiments of the above methods, the one or more biomolecular species is selected from the group consisting of collagen IV, laminin, entactin, integrin, fibronectin, vitronectin, proteoglycans, BM-40/osteonectin/SPARC, BM-90, and bFGF.

In a preferred embodiment of the above methods, the one of more biomolecular species is collagen IV.

In certain embodiments of the above methods, the one or more chemical moieties targeting one or more biomolecular species is a collagen IV-targeting peptide with an amino acid sequence of KLWVLPKGGGC (SEQ ID NO: 1).

In certain embodiments of the above methods, the carrier particles are bound to one or more surfaces of the surgical site.

In certain embodiments of the above methods, the surgical site comprises peritoneal surfaces.

In certain embodiments of the methods, greater than 10 percent of the one or more pharmaceutical compositions is released within 24 hours of membrane formation. In certain embodiments, about 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, or 70% of one or more of the pharmaceutical compositions are released within 24 hours of membrane formation. In a preferred embodiment, about 13.5% or 19.1% of the one or more pharmaceutical compositions are released within 24 hours of membrane formation. In a further preferred embodiment, about 13.5% Dex-Pal and about 19.1% Dex are released within 24 hours of membrane formation.

In certain embodiments of the above methods, the one or more pharmaceutical compositions are released from the composite membrane over a time period of at least 14 days. In certain embodiments, the one or more pharmaceutical compositions are released over a time period of at least 15, 16, 17, 18, 19, 20, 21, 22, 23, 24, 25, 26, 27, 28, 29, 30, 35, 40, 45, or 50 days.

In certain embodiments of the above methods, the targeting particles or the carrier particles bind with the base membrane. In certain embodiments, the base membrane is collagen IV. After binding of the targeting particles or carrier particles with the base membrane, the targeting particles or carrier particles are optionally washed away. In certain embodiments, the targeting particles or carrier particles are optionally washed away with saline. Following this, scaffolding particles are applied to the targeting particles or carrier particles. In certain embodiments, the scaffolding particles interact with the targeting particles or carrier particles by electrostatic or ionic interactions. In certain embodiments, the targeting particles or carrier particles are negatively charged and the scaffolding particles are positively charged. Following this, crosslinking of the scaffolding particles with targeting particles or carrier particles proceeds. In certain embodiments, the crosslinking may be photo-initiated. In certain embodiments, photo-initiated crosslinking comprises the application of UV light. Following this, the scaffolding particles are optionally washed away. In certain embodiments, the scaffolding particles are optionally washed away with saline.

The subject matter described herein is directed to the following embodiments:

1. A method of treating a surgical site comprising:
   contacting the surgical site with a particle formulation comprising targeting particles and scaffolding particles; and
   crosslinking the targeting particles and scaffolding particles to provide a composite membrane at the surgical site, wherein formation of post-surgical adhesions are inhibited by the composite membrane.

2. A method of reducing peritoneal adhesions, wherein said peritoneal adhesions form subsequent to abdominal surgery, said method comprising:
   contacting an abdominal surgical site with targeting particles;
   contacting said targeting particles with scaffolding particles; and
   crosslinking the targeting particles and scaffolding particles to provide a composite membrane at the abdominal surgical site, wherein said peritoneal adhesions are reduced by said composite membrane.

3. The method of embodiment 1 or 2, wherein the targeting particles comprise one or more chemical moieties targeting one or more biomolecular species located at the surgical site.

4. The method of embodiment 3, wherein said one or more biomolecular species is selected from the group consisting of collagen IV, laminin, entactin, integrin, fibronectin, vitronectin, proteoglycans, BM-40/osteonectin/SPARC, BM-90, and bFGF.

5. The method of embodiment 3 or 4, wherein said one of more biomolecular species is collagen IV.

6. The method of embodiment 3, wherein a targeting ligand comprises the one or more chemical moieties.

7. The method of embodiments 1 or 2, wherein the targeting particles and/or scaffolding particles are nanoparticles, microparticles or mixtures thereof.

8. The method of any one of embodiments 1, 2, or 7, wherein the targeting particles and scaffolding particles are nanoparticles.

9. The method of embodiment 1 or 2, wherein the targeting particles further comprise one or more pharmaceutical compositions.

10. The method of embodiment 9, wherein said one or more pharmaceutical compositions is selected from the group consisting of dexamethasone, dexamethasone 21-Palmitate, and a combination thereof.

11. The method of embodiment 9 or 10, wherein the one or more pharmaceutical compositions inhibit tissue inflammation.

12. The method of embodiment 11, wherein the presence of inflammatory cytokines and/or chemokines at the surgical site is reduced.

13. The method of embodiment 9, further comprising releasing the one or more pharmaceutical compositions from the composite membrane.

14. The method of embodiment 13, wherein greater than 10 percent of the one or more pharmaceutical compositions is released within 24 hours of membrane formation.

15. The method of embodiment 13, wherein the one or more pharmaceutical compositions is released over a time period of at least 14 days.

16. The method of embodiment 1 or 2, wherein the scaffolding particles are non-hydrogel particles.

17. The method of embodiment 1 or 2, wherein the scaffolding particles comprise a core-shell architecture.

18. The method of embodiment 1, 2, or 17, wherein said scaffolding particles comprise a poly(lactic-co-glycolic acid) core and a polyethyleneimine shell.

19. The method of embodiment 1 or 2, wherein the targeting particles comprise a poly(ethylene glycol)-poly(lactic-co-glycolic acid) block polymer.

20. The method of embodiment 1 or 2, wherein the targeting particles and scaffolding particles interact with one another via ionic or electrostatic interactions prior to crosslinking.

21. The method of any one of embodiments 1, 2, or 20, wherein the targeting particles and scaffolding particles are oppositely charged.

22. The method of embodiment 1 or 2, wherein the crosslinking is photo-initiated.

23. The method of embodiment 22, wherein the photo-initiated crosslinking comprises the application of UV light.

24. The method of embodiment 23, wherein the UV light has a wavelength of about 365 nm.

25. The method of embodiment 1 or 2, wherein the scaffolding particles comprise one or more photolabile groups.

26. The method of embodiment 25, wherein the one or more photolabile groups is a diazirine functional group.

27. The method of embodiment 1 or 2, wherein the composite membrane is biodegradable.

28. The method of embodiment 1 or 2, wherein the surgical site comprises peritoneal surfaces.

29. The method of embodiment 1, wherein the targeting particles are applied to the surgical site prior to application of the scaffolding particles to the surgical site.

30. The method of embodiment 1 or 2, wherein the targeting particles are bound to one or more surfaces of the surgical site.

31. The method of embodiment 1 or 2, wherein said targeting particles comprise one or more chemical moieties targeting one or more biomolecular species, wherein said one or more biomolecular species is collagen IV, wherein said targeting particles comprise a poly(ethylene glycol)-poly(lactic-co-glycolic acid) block polymer, and the targeting particles further comprise one or more pharmaceutical compositions, wherein said pharmaceutical compositions are dexamethasone and dexamethasone 21-Palmitate; and said scaffolding particles comprise a poly(lactic-co-glycolic acid) core and a polyethyleneimine shell and are further functionalized with one or more photolabile groups, wherein said one or more photolabile groups is a diazirine functional group.

32. A method of treating a surgical site comprising:
contacting the surgical site with a particle formulation comprising scaffolding particles and carrier particles transporting one or more pharmaceutical compositions; and
crosslinking the carrier particles and scaffolding particles to provide a composite membrane at the surgical site, wherein formation of post-surgical adhesions are inhibited by the composite membrane.

33. A method of reducing peritoneal adhesions, wherein said peritoneal adhesions form subsequent to abdominal surgery, said method comprising:
contacting an abdominal surgical site with carrier particles;
contacting said carrier particles with scaffolding particles; and
crosslinking the carrier particles and scaffolding particles to provide a composite membrane at the abdominal surgical site, wherein said peritoneal adhesions are reduced by said composite membrane.

34. The method of embodiment 33, wherein said carrier particles transport one or more pharmaceutical compositions.

35. The method of any one of embodiments 32-34, wherein the one or more pharmaceutical compositions inhibit tissue inflammation.

36. The method of embodiment 35, wherein said one or more pharmaceutical compositions is selected from the group consisting of dexamethasone, dexamethasone 21-Palmitate, and a combination thereof.

37. The method of embodiment 35, wherein the presence of inflammatory cytokines and/or chemokines at the surgical site are reduced.

38. The method of any one of embodiments 32-34, further comprising releasing the one or more pharmaceutical compositions from the composite membrane.

39. The method of embodiment 38, wherein the one or more pharmaceutical compositions is released over a time period of at least 14 days.

40. The method of embodiment 32 or 33, wherein the scaffolding particles are non-hydrogel particles.

41. The method of embodiment 32 or 33, wherein the scaffolding particles and/or carrier particles are nanoparticles, microparticles or mixtures thereof.

42. The method of embodiment 32, 33, or 41, wherein the carrier particles and scaffolding particles are nanoparticles.

43. The method of embodiment 32 or 33, wherein the carrier particles and scaffolding particles interact with one another via ionic or electrostatic interactions prior to crosslinking.

44. The method of any one of embodiments 32, 33, or 43, wherein the carrier particles and scaffolding particles are oppositely charged.

45. The method of embodiment 32 or 33, wherein the crosslinking is photo-initiated.

46. The method of embodiment 45, wherein the photo-initiated crosslinking comprises the application of UV light.

47. The method of embodiment 46, wherein the UV light has a wavelength of about 365 nm.

48. The method of embodiment 32 or 33, wherein the scaffolding particles or carrier particles comprise one or more photolabile groups.

49. The method of embodiment 48, wherein the one or more photolabile groups is a diazirine functional group.

50. The method of embodiment 32 or 33, wherein the composite membrane is biodegradable.

51. The method of embodiment 32 or 33, wherein the carrier particles comprise one or more chemical moieties targeting one or more biomolecular species located at the surgical site.

52. The method of embodiment 51, wherein said one or more biomolecular species is selected from the group consisting of collagen IV, laminin, entactin, integrin, fibronectin, vitronectin, proteoglycans, BM-40/osteonectin/SPARC, BM-90, and bFGF.

53. The method of embodiment 52, wherein said one of more biomolecular species is collagen IV.

54. The method of embodiment 32 or 33, wherein the carrier particles are bound to one or more surfaces of the surgical site.

55. The method of embodiment 32 or 33, wherein the surgical site comprises peritoneal surfaces.

56. A kit comprising:
    (i) a vial containing a first particle formulation comprising targeting particles; and
    (ii) a vial containing a second particle formulation comprising scaffolding particles.

57. A kit comprising:
    (i) a vial containing a first particle formulation comprising carrier particles; and
    (ii) a vial containing a second particle formulation comprising scaffolding particles.

58. A composition comprising targeting particles and scaffolding particles.

59. A composition comprising carrier particles and scaffolding particles.

60. A composite membrane formed by crosslinking a first particle composition comprising targeting particles with a second particle composition comprising scaffolding particles.

61. A composite membrane formed by crosslinking a first particle composition comprising carrier particles with a second particle composition comprising scaffolding particles.

The disclosed subject matter is further described in the following non-limiting Examples. It should be understood that these Examples, while indicating preferred embodiments of the invention, are given by way of illustration only.

Example 1—Composite Membrane for Inhibiting Post-Surgical Adhesions

Here we report the development of a biologically targeted, photo-crosslinkable nano-patch (pCNP) for postsurgical adhesion prevention. pCNP is comprised of two NPs. The first NP (NP-A) is designed to carry the anti-inflammatory cargo and specifically bind to the injured site. Since the hallmark of injured epithelial/mesothelial surfaces is exposed basement membranes, and a component of basement membrane is collagen IV, we chose to target NP-A against collagen IV. The second NP (NP-B) is designed with a positively charged surface, opposite to that of NP-A, to enable absorption to the layer of NP-A through ionic interactions (FIG. 1A). The two NPs can be subsequently crosslinked by UV-irradiation through diazirine reactive group to form a nano-patch. The pCNP was designed to be administered intraperitoneally in sequence (FIG. 1B). First, a suspension of NP-A is incubated at the site of injury to allow for specific binding to the basement membrane, which is exposed following mesothelial damage. Particle properties that afford a stable suspension for administration would result in an insufficiently low-density barrier when a single particle is administered due to steric and ionic hindrance. Thus, a suspension containing NP-B is subsequently administered to rapidly form a dense layer through ionic adsorption between the oppositely charged NP-A and NP-B. The injured site is then irradiated with UV light with a wavelength of 365 nm to initiate crosslinking of the two nanoparticles, forming a specific and dense biological barrier between the injured peritoneal surfaces.

Formulation and Characterization of pCNP

NP-A was formulated using a poly(ethylene glycol)-poly (lactic-co-glycolic acid) block copolymer (PEG-PLGA), which was functionalized with a collagen IV-targeting peptide. Dexamethasone 21-Palmitate (Dex-Pal), an anti-inflammatory agent to prevent adhesion formation, was encapsulated into NP-A with the loading amount of 65.2±4.02 µg/mg. Physical characterization of NP-A demonstrated a spherical morphology with an average hydrodynamic diameter of 166.1±1.8 nm and a negatively charged surface of −12.1±0.3 mV. NP-B was formulated to contain a PLGA-PEG core and a branched polyethyleneimine (PEI) shell. The surface of NP-B was functionalized to display diazirine groups to allow photo-induced crosslinking among NPs. NP-B was characterized with an average hydrodynamic diameter of 175.1±28.7 nm and a positively charged surface of 23.0±3.0 mV.

To confirm the ability of pCNP to form a nano-patch, we first verified the crosslinking reaction between NP-A and NP-B using photo-DSC analysis (FIG. 2A-FIG. 2C). We found that the peak of reaction emerged around 1.5 minutes after the exposure of UV irradiation and the reaction was complete within 10 minutes. The heat of the reaction appeared to be dependent on the concentration of NP-B, and thus the diazirine groups. Notably, no detectable heat was produced in water without NP-A or NP-B by UV irradiation.

pCNP Forms a High-Density Nano-Patch on Collagen IV-Enriched Surface In Vitro

Figure 3R:
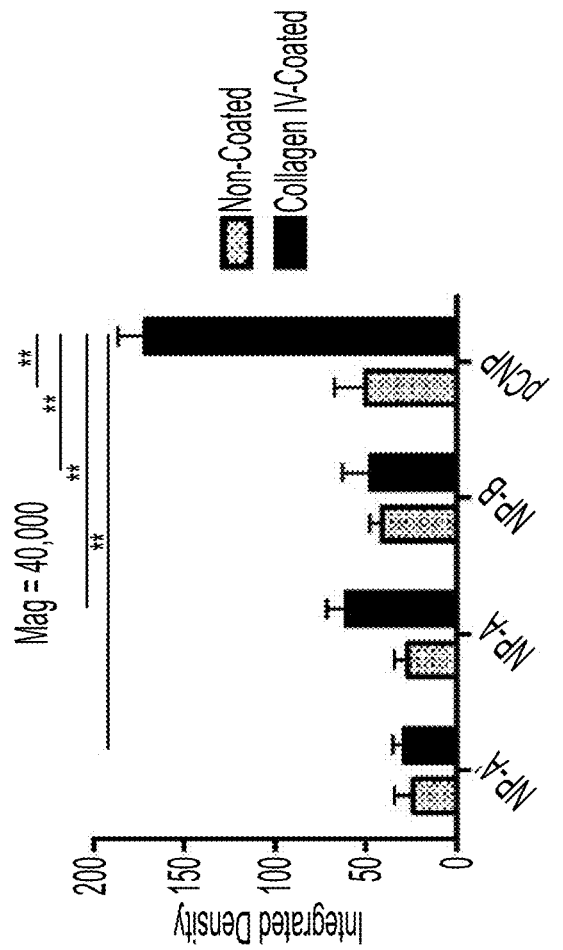
FIG. 3R shows the integrated density of gray value in e-h, m-p and FIG. 2A-2C. Data represents mean±standard error of the mean (SEM) (n=3). *P<0.05, **P<0.01.
Figure 3Q:
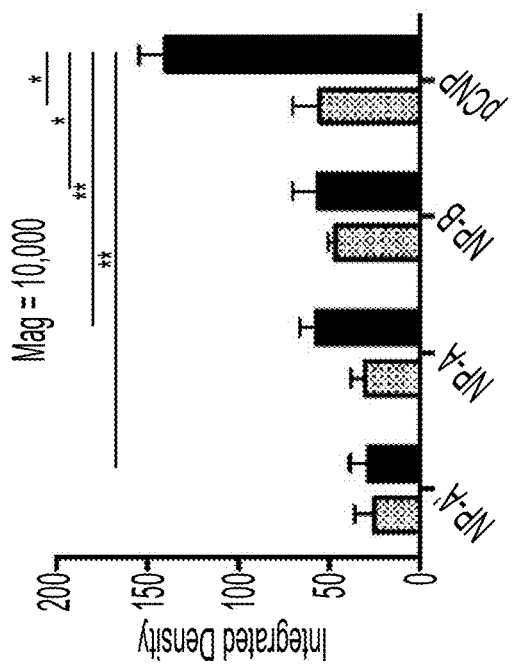
FIG. 3Q shows the integrated density of gray value in a-d, i-l and FIG. 2A-2C. Data represents mean±standard error of the mean (SEM) (n=3). *P<0.05, **P<0.01.
Figure 4A:
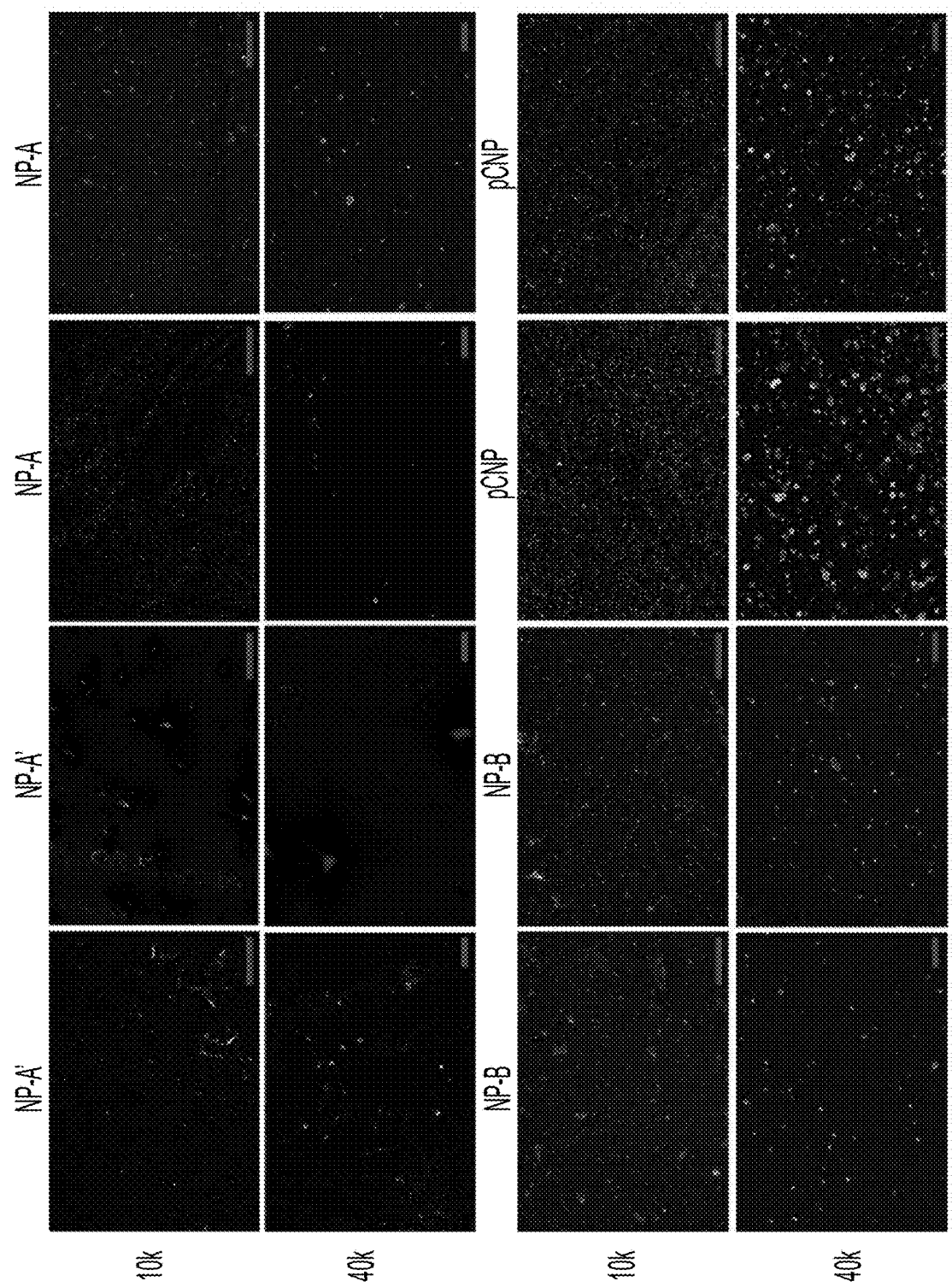
FIG. 4A depicts repeated FESEM images showing the formation of a nano-patch on non-coated glass cover slides using different approaches.
Figure 4B:
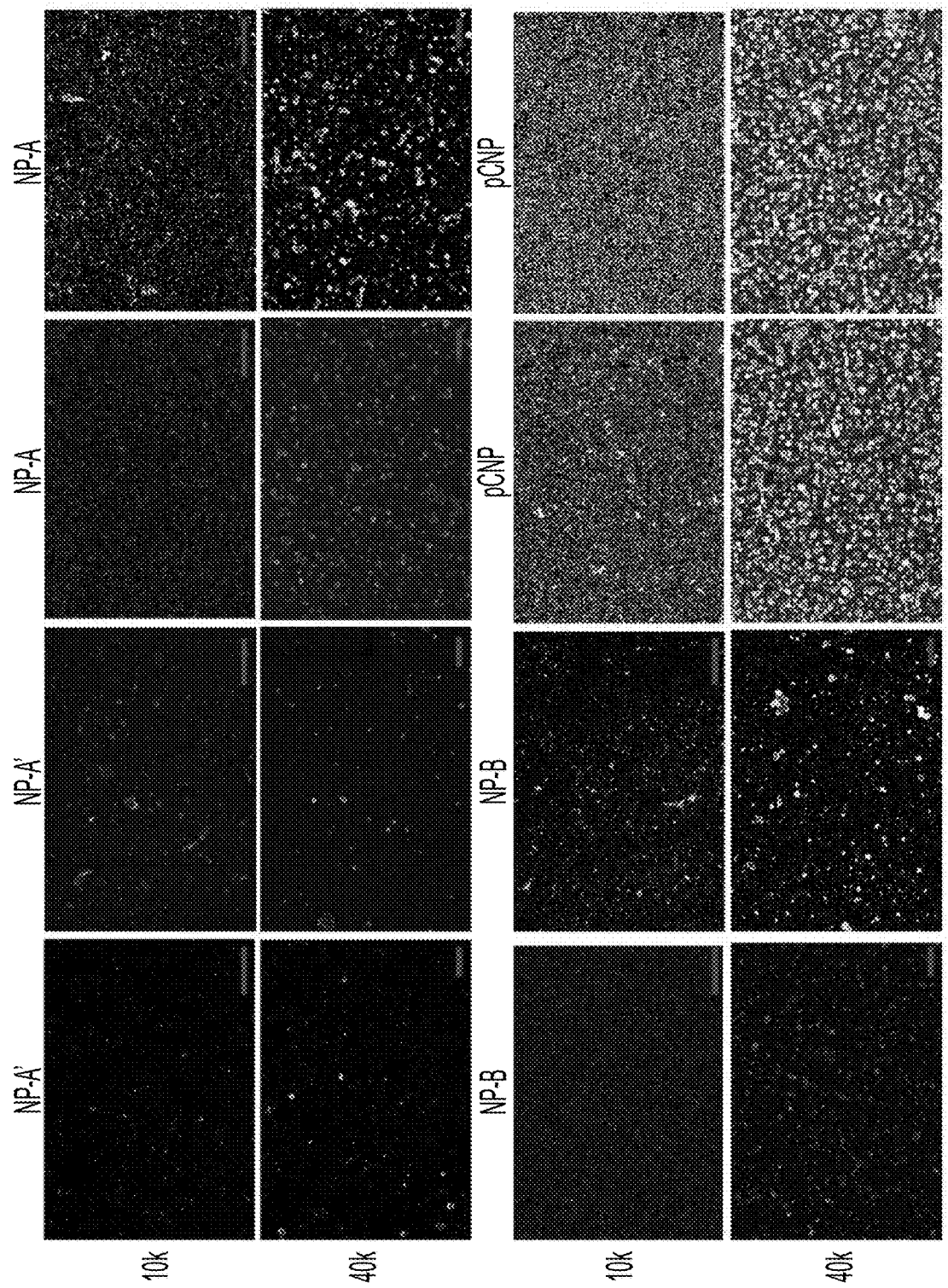
FIG. 4B shows repeated FESEM images showing the formation of a nano-patch on collagen IV-coated glass cover slides using different approaches.

We then demonstrated that the NP regimen can form a dense and stable nano-patch in a biologically targeted fashion in vitro. NPs were applied to non-coated or collagen IV-coated glass slides and formation of nano-patch was examined. A collagen IV surface was used to simulate injured peritoneal surfaces, as collagen IV is one of the major constituents of basement membrane. The density of the nano-patch was confirmed by FESEM (FIG. 3a-FIG. 3p, FIG. 4A and FIG. 4B) and quantified using the integrated gray value of the FESEM images (FIG. 3Q, FIG. 3R). We found that nano-patch density formed by biologically targeted NPs (NP-A) was ~2.1 times (average times of integrated density of gray value in 10 k and 20 k magnified FESEM images) higher than that of non-targeted (NP-A') on collagen-IV coated surface. Additionally, the density of pCNP on collagen-IV coated surface was ~2.6 times higher than that of NP-A only and ~3.1 times higher than NP-B only, indicating that pCNP was more efficient in forming high nano-patch density than either of its constituent NPs. The density of pCNP on collagen IV-coated surface was ~3.0 times higher than that on non-coated surface, showing the specificity of pCNP to collagen IV-enriched surface. Here, both NP-A and NP-B bind with the collagen IV coated surface. The layer of NP-A is formed by specific binding between NP-A and collagen IV. The layer of NP-B is formed by photo-crosslinking between NP-B and collagen IV. However, either NP-A or NP-B suffers low density due to steric and ionic hindrance, which is consistent with our hypothesis. Therefore, both NP-A and NP-B are required to form an effective nano-patch barrier. Our findings demonstrated the importance of the targeting ligand, the presence of NP-B, and UV-induced crosslinking in achieving a high nano-patch density.

The Release Profile and the Safety of pCNP In Vitro

Figure 5:
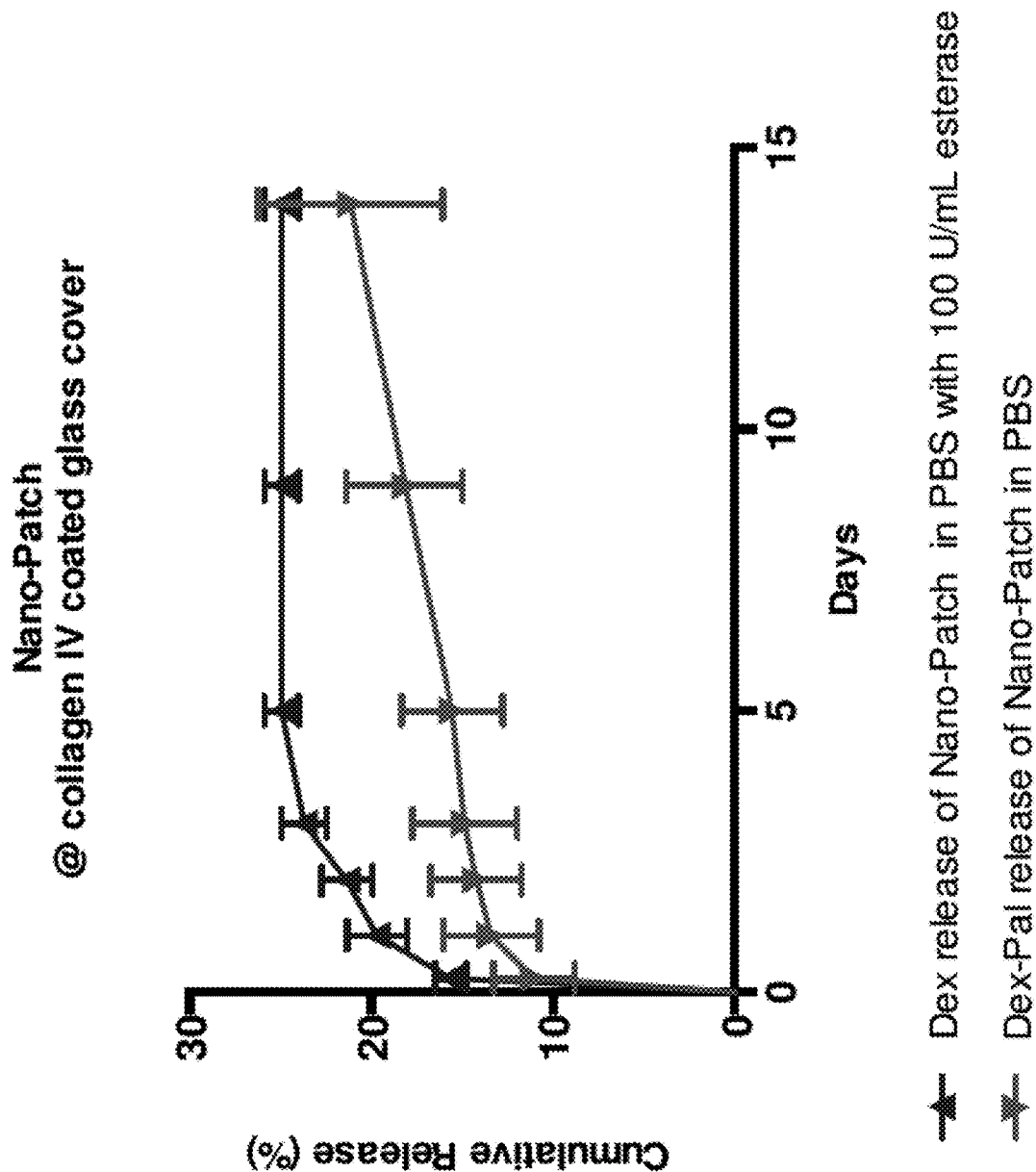
FIG. 5 shows the release profile of dexamethasone (Dex) and dexamethasone 21-Palmitate (Dex-Pal) from pCNP on collagen IV-coated glass cover in PBS at 37° C.
Figure 6:
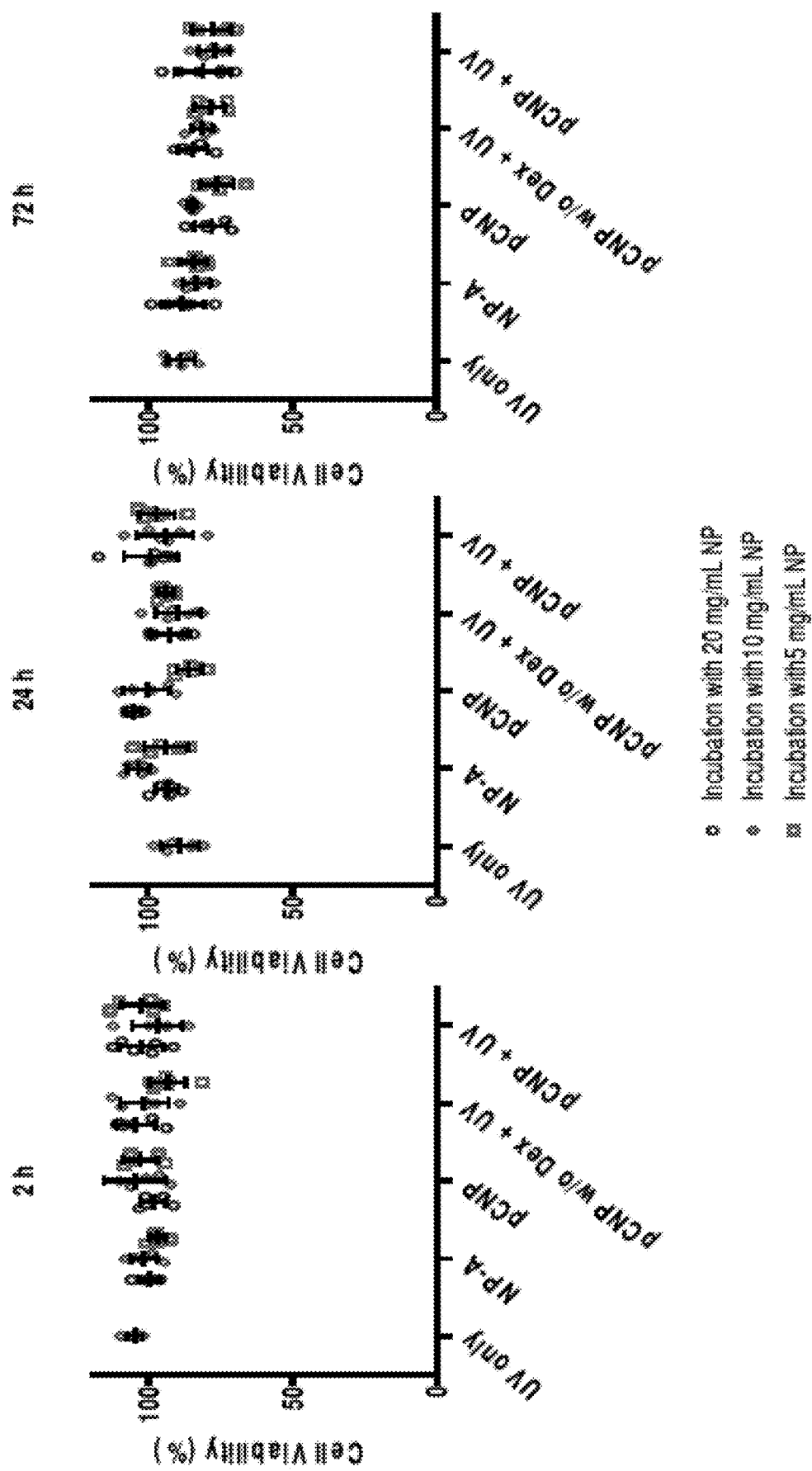
FIG. 6 shows the cell viability of NIH/3T3 fibroblast cells after treating with UV irradiation and/or pCNP on collagen IV-coated 96-well plate.
Figure 7:
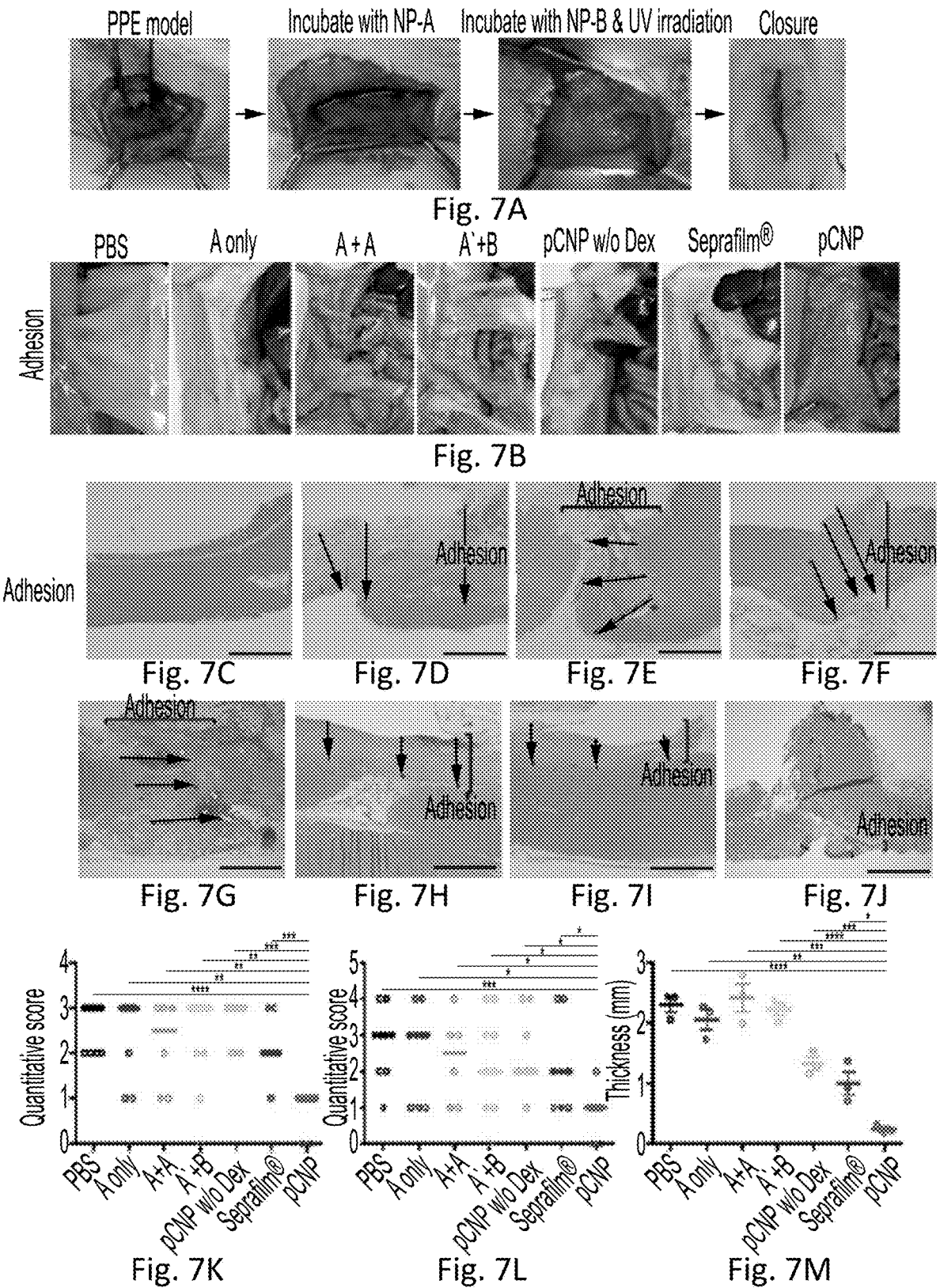
FIG. 7A-FIG. 7M demonstrate how pCNP prevents postsurgical peritoneal adhesion in parietal peritoneal excision (PPE) model in rats.
Figure 8:
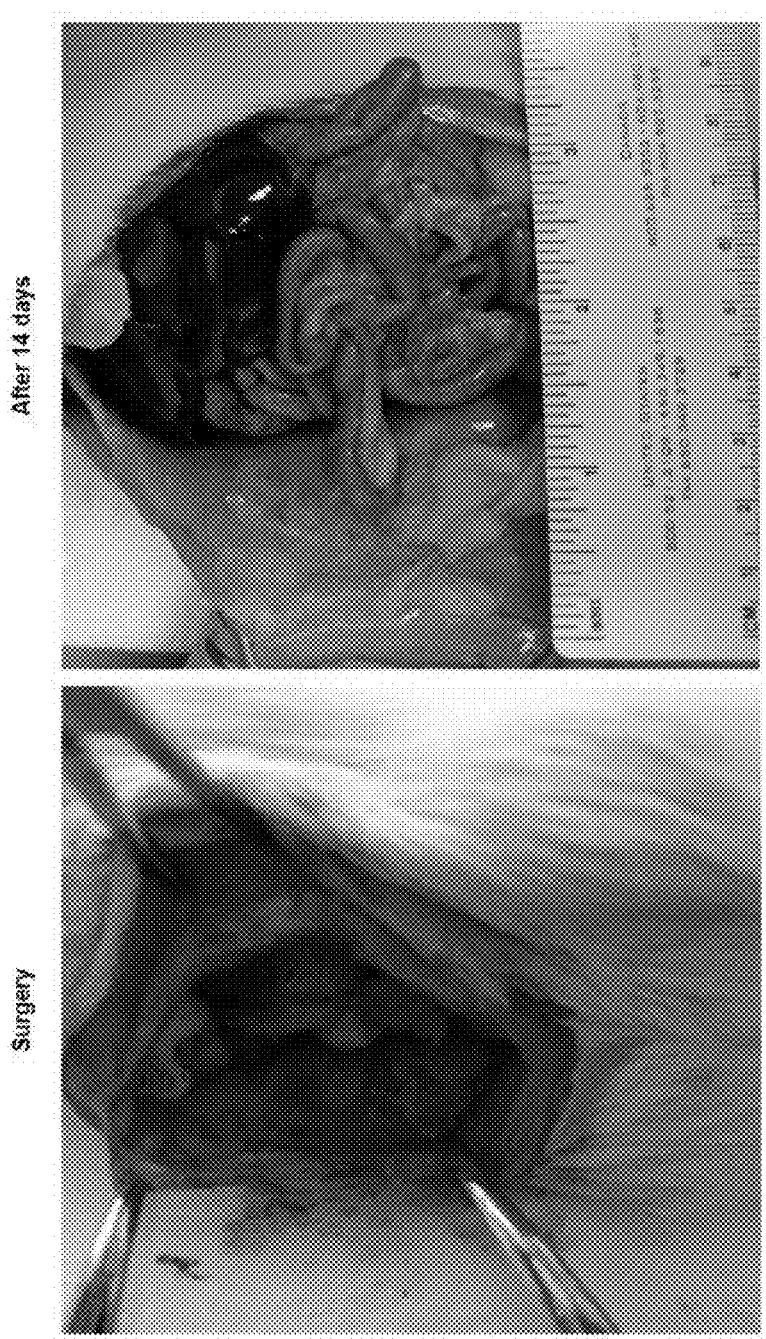
FIG. 8 depicts photos of a parietal peritoneum excision (PPE) rat model showing injured area during abdominal surgery and adhesion after 14 days.
Figure 9:
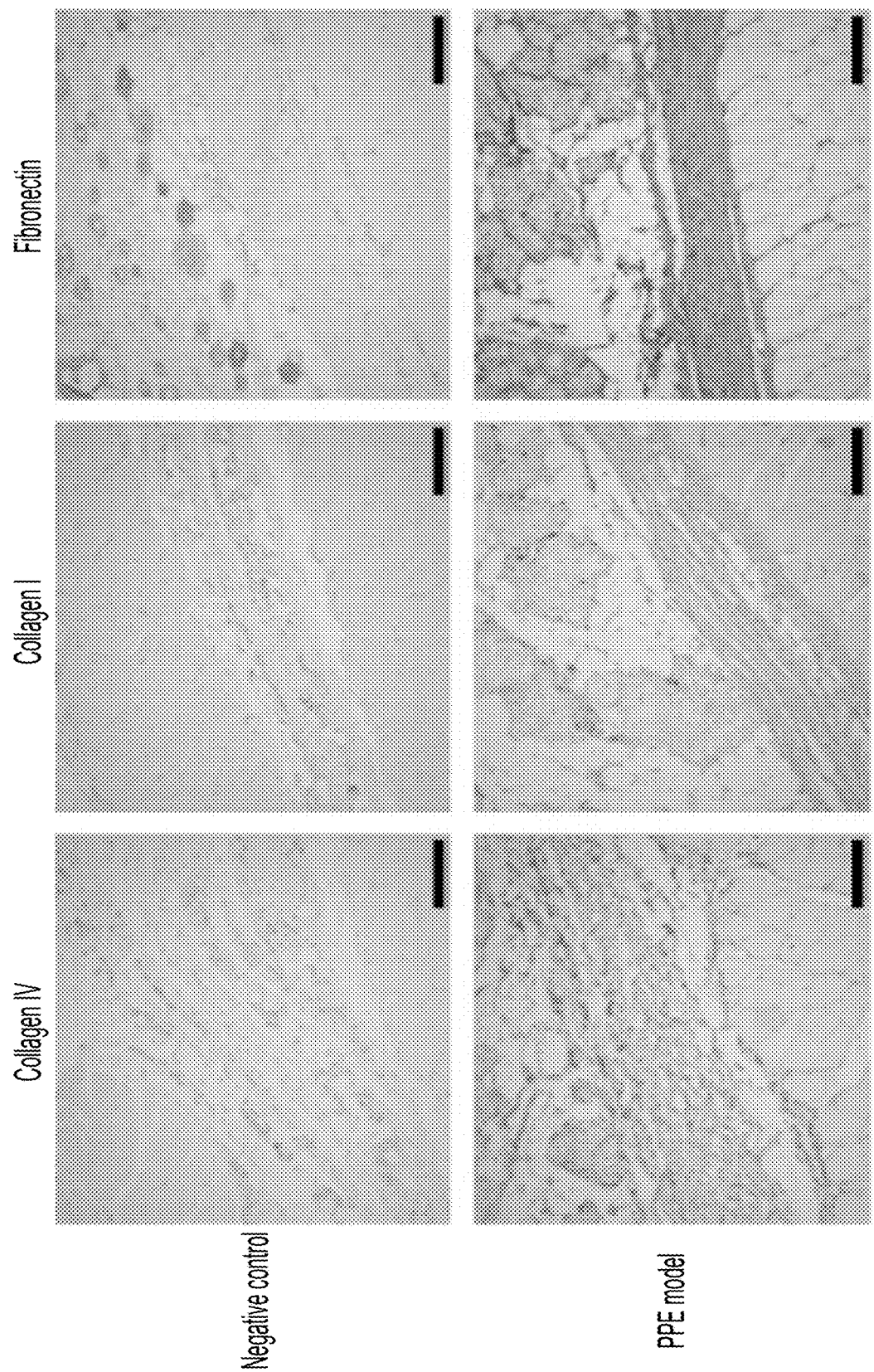
FIG. 9 shows a representative immunohistochemistry (IHC) analysis of a rat abdominal wall in a parietal peritoneum excision (PPE) model. Scale bar=200 μm.
Figure 10A:
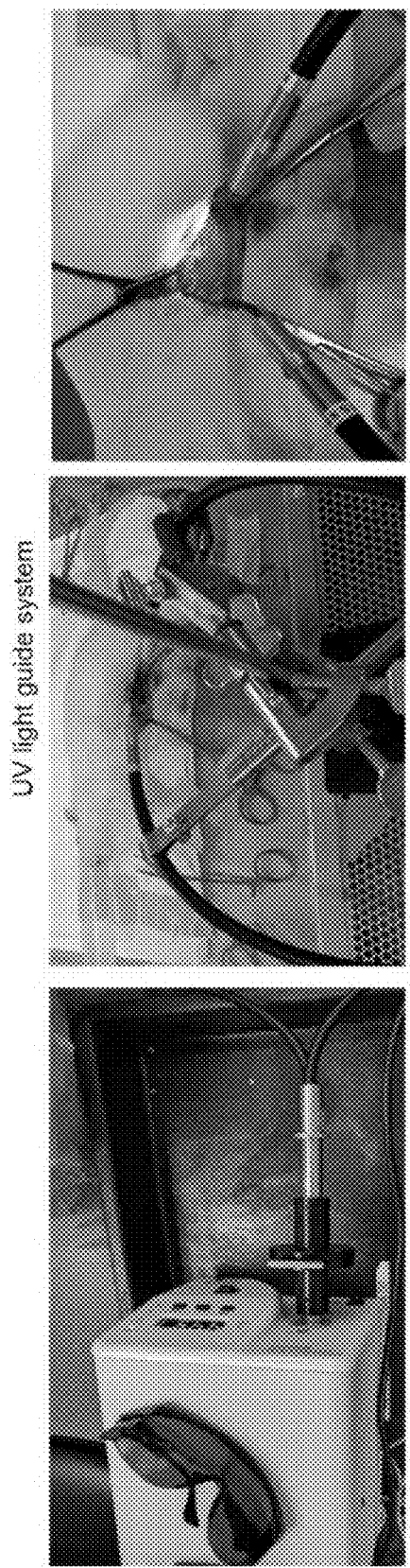
FIG. 10A depicts photos showing the UV light guide apparatus used during postsurgical treatment.
Figure 10B:
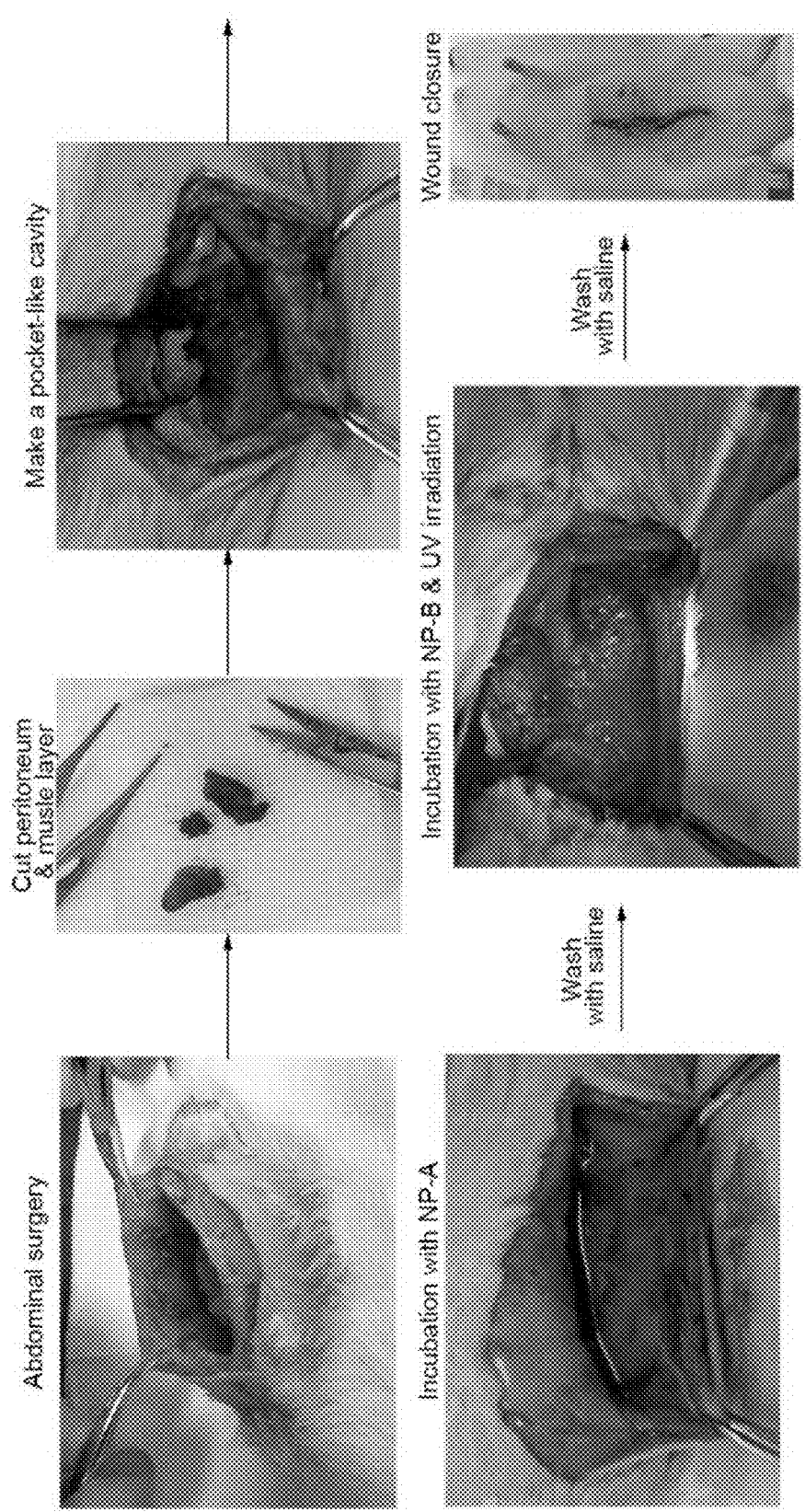
FIG. 10B depicts photos showing the surgery process and the administration of pCNP.

The pCNP was formed on collagen IV-coated glass cover and incubated in PBS at 37° C. The release of Dex-Pal and its active form drug dexamethasone (Dex) was tested with or without the emergence of esterase (FIG. 5). A burst release of 13.5% for Dex-Pal and 19.1% for Dex was observed within 24 h, which can reduce inflammation. The sustained release of Dex-Pal and Dex over two weeks would further provide anti-inflammation during the healing process. To confirm the safety of pCNP, we performed MTS assay using NIH/3T3 fibroblast cells on collagen IV-coated 96-well plate. The cell viability at 2 h, 24 h, 72 h after treatment by pCNP with or without UV irradiation was above ~80% (FIG. 6), indicating a safe usage of pCNP as well as the UV irradiation.

pCNP Prevents Postsurgical Peritoneal Adhesion in Parietal Peritoneal Excision (PPE) Model in Rats We examined the pCNP's ability to prevent postsurgical peritoneal adhesion in vivo (FIG. 7A-FIG. 7M). The rat parietal peritoneum excision (PPE) model was utilized to study postsurgical adhesion (FIG. 8). Survival surgery was carried out to excise a ~2×5 cm patch of peritoneum with the underlying muscle layer from the left abdominal wall. We performed immunohistochemistry (IHC) analysis of the abdominal wall in rat PPE model and showed the injured peritoneal surfaces indeed exposes collagen IV, collagen I and fibronection (FIG. 9). Such finding indicated that our strategy of targeting collagen IV was feasible. Following excision, rats were laid on the side ipsilateral to the excision site in order to expose the injured cavity for NP incubation. A solution of NP-A was administered to the peritoneal cavity and incubated for 10 minutes. After NP-A solution was removed, the peritoneal cavity was washed twice with saline. Following NP-A, NP-B was administered and incubated for 10 minutes under UV irradiation. The peritoneal cavity was then washed twice more with saline. The abdominal surgical wound was then closed with sutures. (FIG. 7A, FIG. 10A and FIG. 10B). Control experimental groups included saline incubation (PBS group), NP-A only (A only), NP-A+NP-A incubation (A+A), non-targeted NP-A with NP-B and UV crosslinking (A'+B), pCNP without encapsulating Dex-Pal (pCNP w/o Dex), and a commercially available adhesion barrier Seprafilm®. To assess the quality and quantity of postsurgical adhesions, a second-look laparotomy was performed 14 days post surgery. Adhesions were graded based on a previously described scoring system.

Figure 11A:
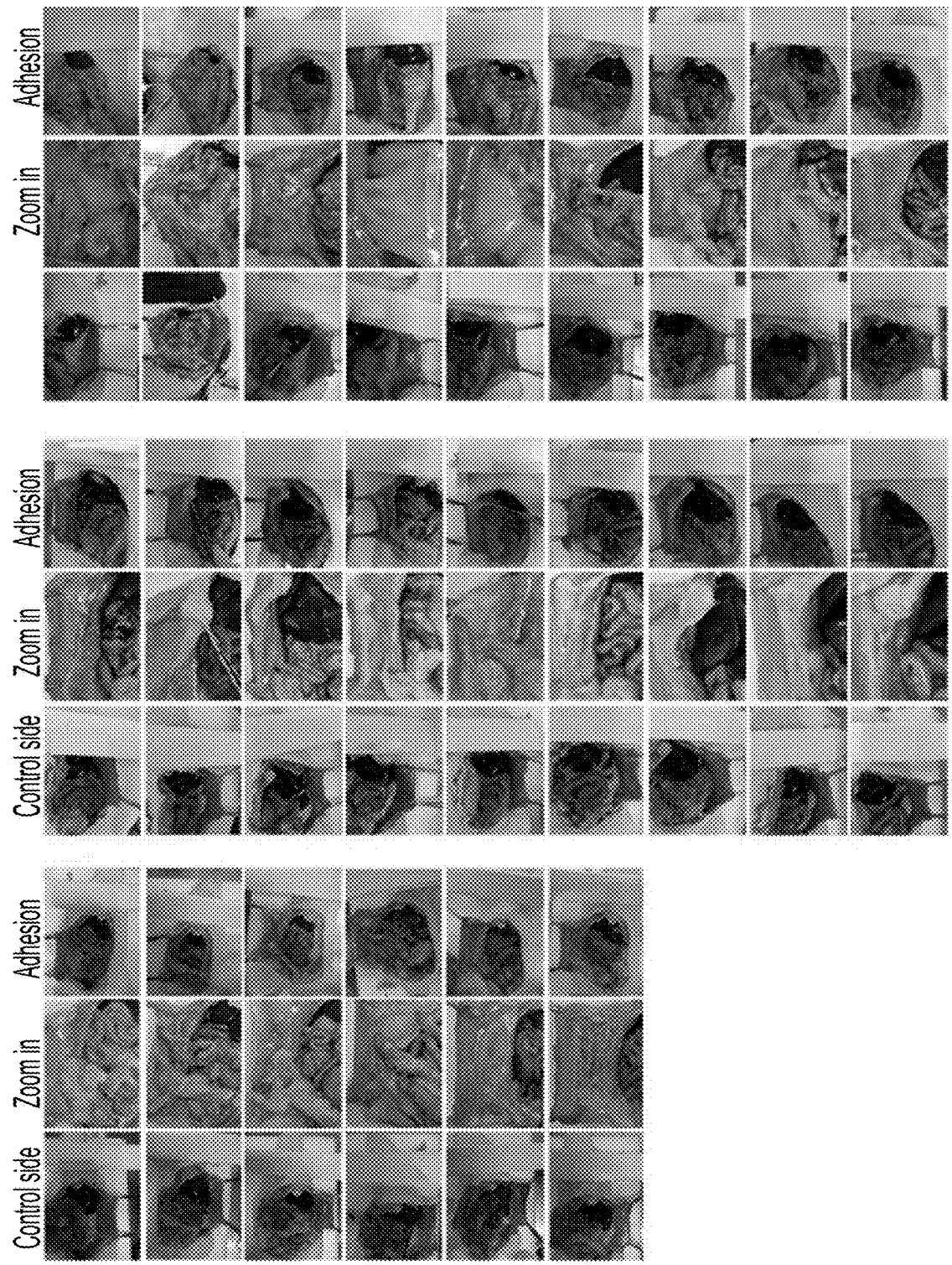
FIG. 11A shows postsurgical peritoneal adhesion on rats in each of the experimental groups 14 days after treatments.
Figure 11B:
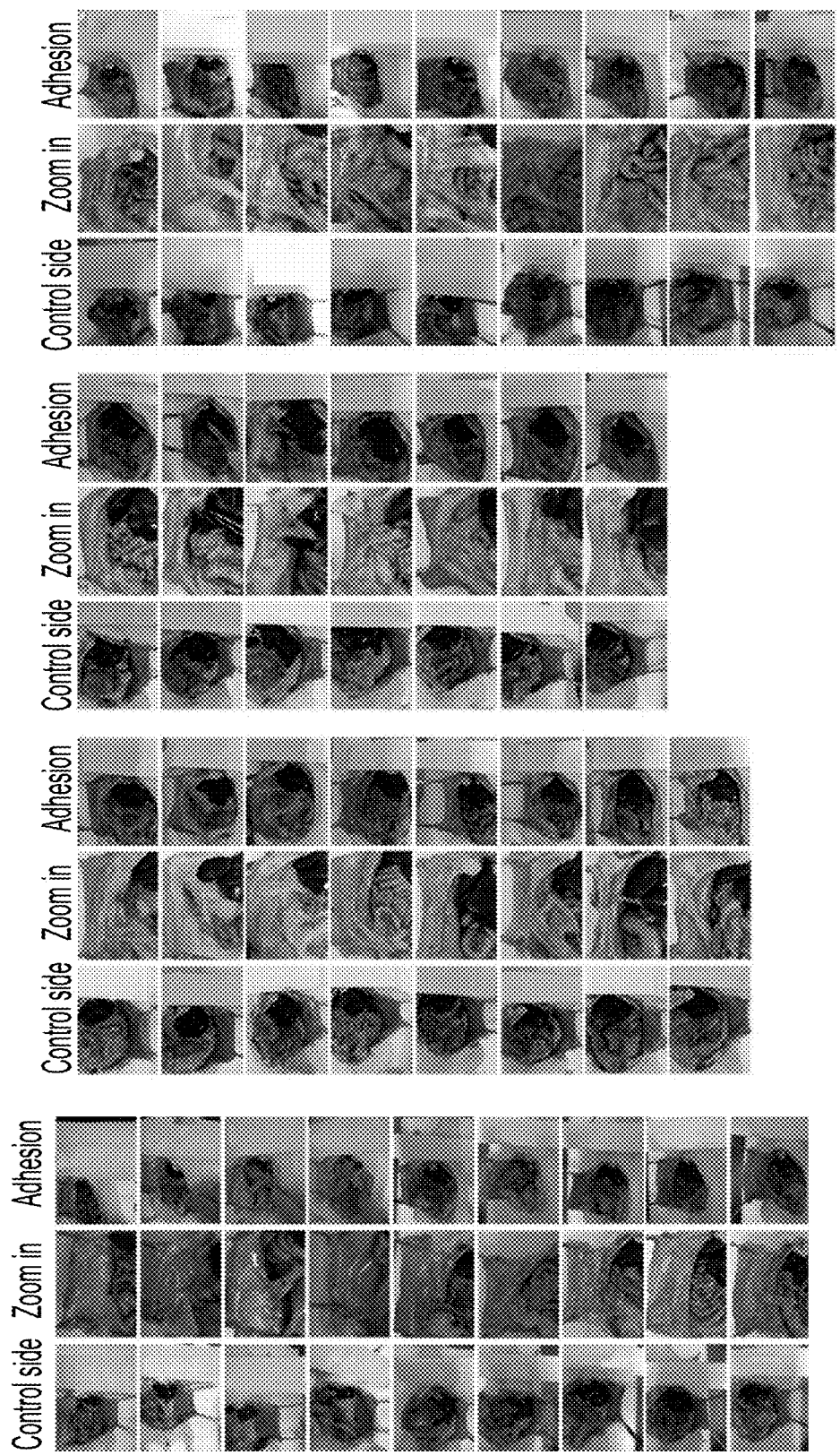
FIG. 11B shows postsurgical peritoneal adhesion on rats in each of the experimental groups 14 days after treatments.
Figure 12:
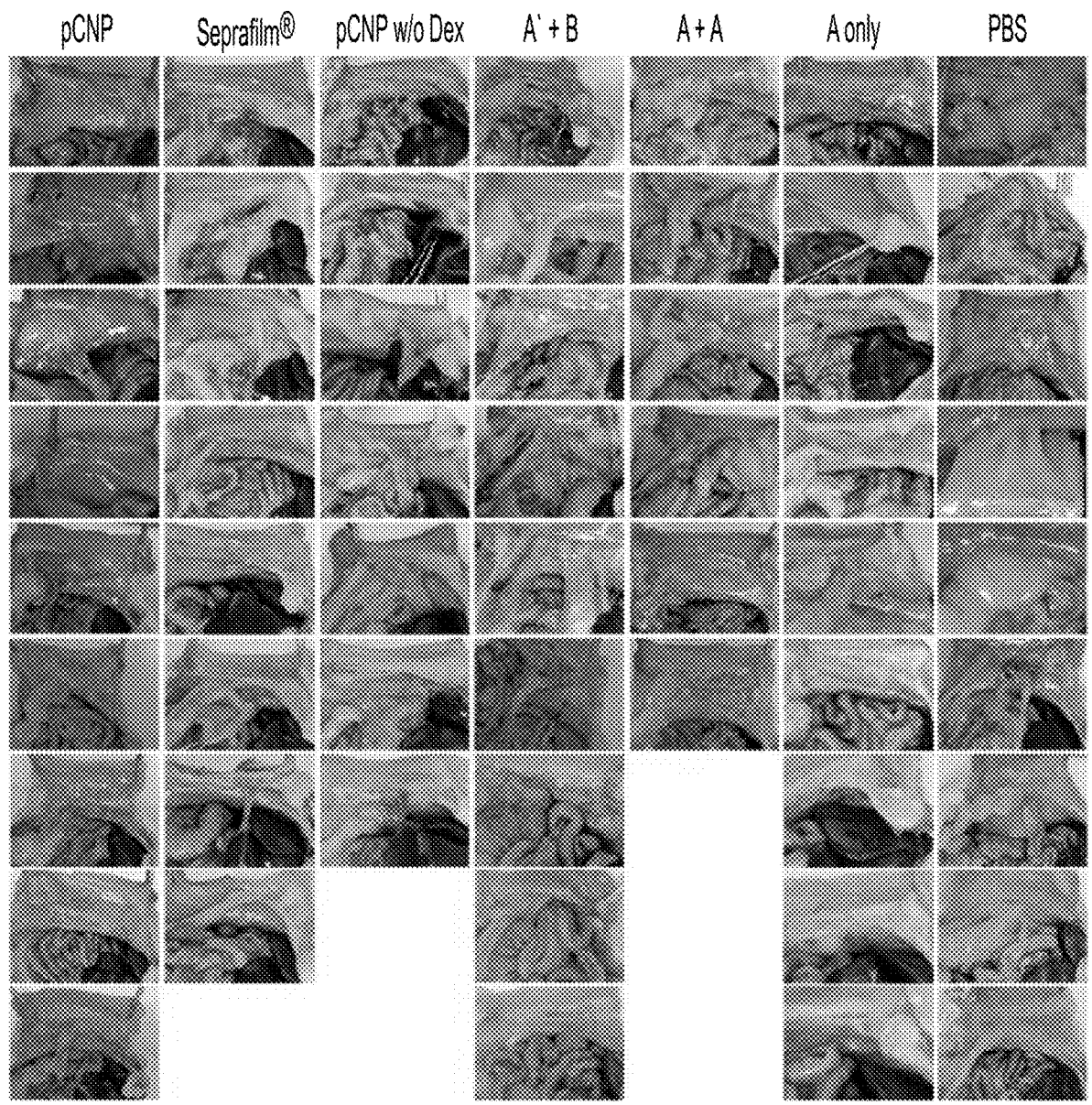
FIG. 12 shows zoomed in views of the postsurgical peritoneal adhesion on rats 14 days after treatments.
Figure 13:
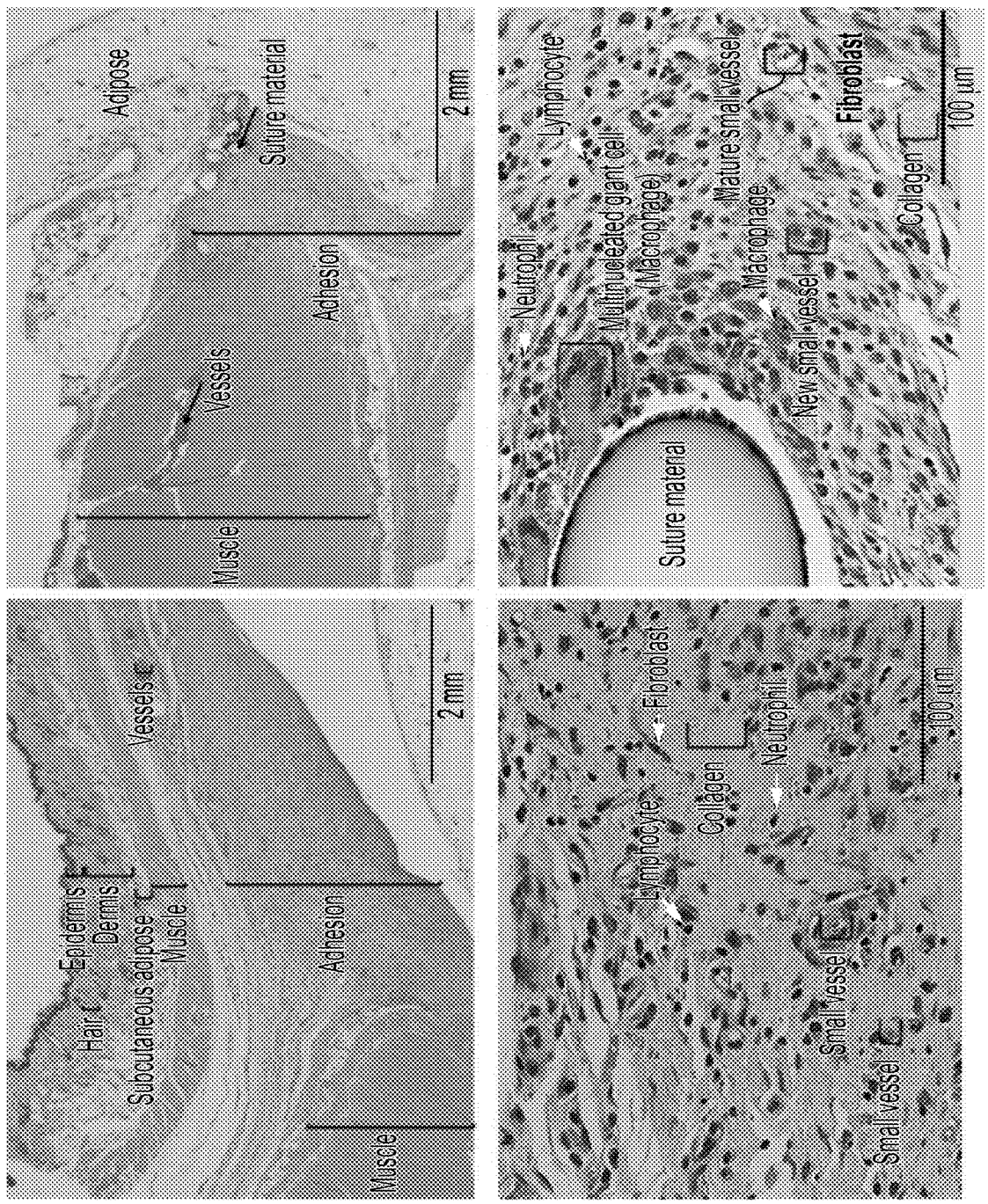
FIG. 13 depicts representative H&E staining histology tissue images showing muscle and adhesion/fibrosis after abdominal surgery. For (a) and (b), scale bar=2 mm; For (c) and (d), scale bar=100 μm.
Figure 14:
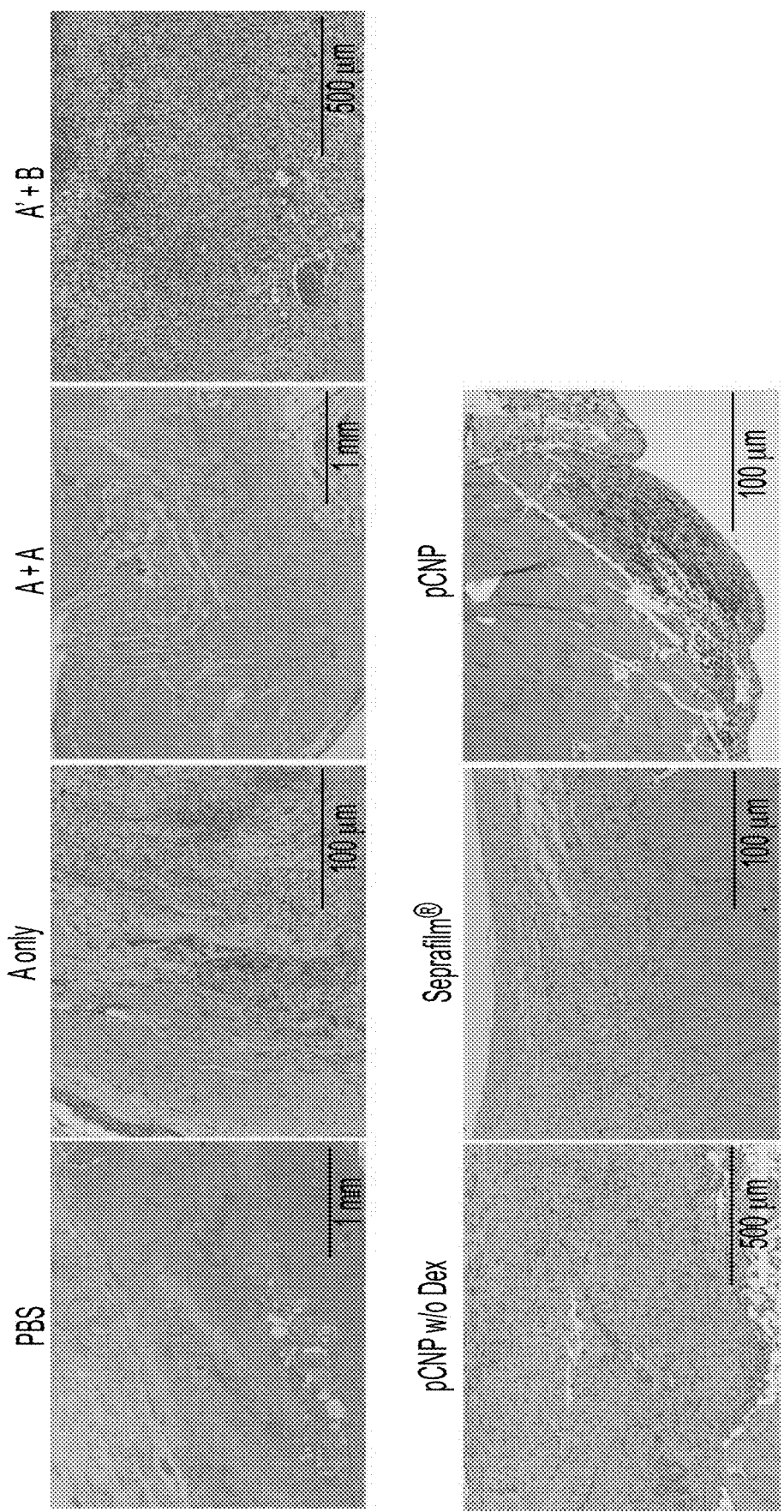
FIG. 14 depicts representative H&E staining histology tissue images showing the adhesion/fibrosis after treatments. For PBS and A+A group, scale bar=1 mm; for others, scale bar=500 μm.

As seen in FIG. 7B, the PPE model induces strong postsurgical adhesions in the PBS control group. In contrast, minimal adhesion was seen in rats treated with pCNP (FIG. 7B, FIGS. 11 and 12). The other experimental groups (A only, A+A, A'+B, pCNP w/o Dex, Seprafilm®) all demonstrated intermediate levels of adhesion prevention. The levels of adhesions were quantified using a four-point scale qualitative scoring system (FIG. 7K). We demonstrated that pCNP is the most effective in preventing adhesions with a median score of 1, followed by Seprafilm® (2), A+A (2.5). We also assessed the quality of adhesions with a 5-point quantitative scoring system (FIG. 7L). Similar to the quantity scores, the pCNP treatment was the most effective at preventing adhesions (median score of 1) and PBS was the least effective. All of the NP-A containing groups were able to reduce the adhesions, likely due to the effects of dexamethasone that was encapsulated within the NPs. Importantly, our observations that pCNP is significantly more effective than NP-A+NP-A, NP-A'+NP-B and pCNP w/o Dex demonstrate the importance of crosslinking with NP-B, biological targeting and controlled release of Dex-Pal, respectively. Taken all together, the properties of pCNP made it more efficient in preventing postsurgical peritoneal adhesion than the commercially used adhesion barrier Seprafilm® in rat PPE model.

To further quantify the levels of adhesions, we examined the adhesions histologically (FIG. 7C-FIG. 7J, FIGS. 13 and 14). To compare the adhesions in rats between the different treatments, we randomly selected three positions in the histological images and measured the thickness of adhesion/fibrosis. The average thickness of adhesion was 2.31±0.13 mm in PBS group, 2.05±0.17 mm in NP-A only group, 2.41±0.23 mm in NP-A plus NP-A group, 2.23±0.11 mm in NP-A' plus NP-B group, 1.32±0.11 in pCNP w/o Dex group, 1.00±0.19 in Seprafilm® group, and 0.24±0.04 mm in pCNP group (FIG. 7M). We demonstrated that pCNP was the most effective treatment in inhibiting postsurgical adhesion with minimal fibrosis in the areas of injury.

pCNP Shows Low Toxicity in Parietal Peritoneal Excision (PPE) Model in Rats

Figures 15A, 15B, 15C:
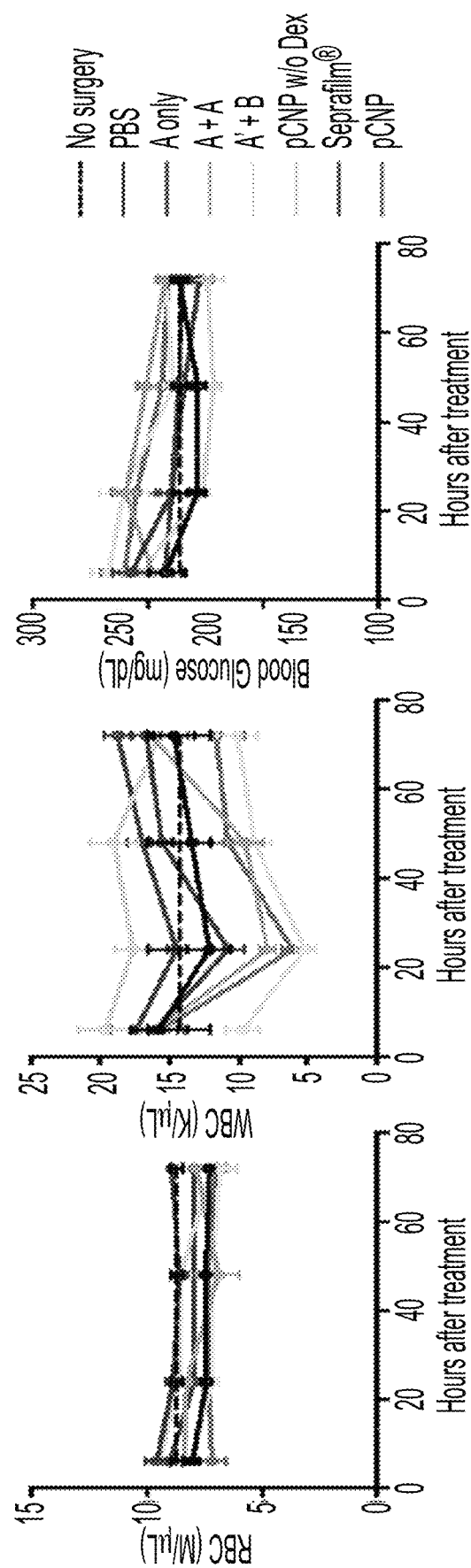
FIG. 15A-15C demonstrate how pCNP shows low toxicity in a parietal peritoneal excision (PPE) model in rats.
Figure 16:
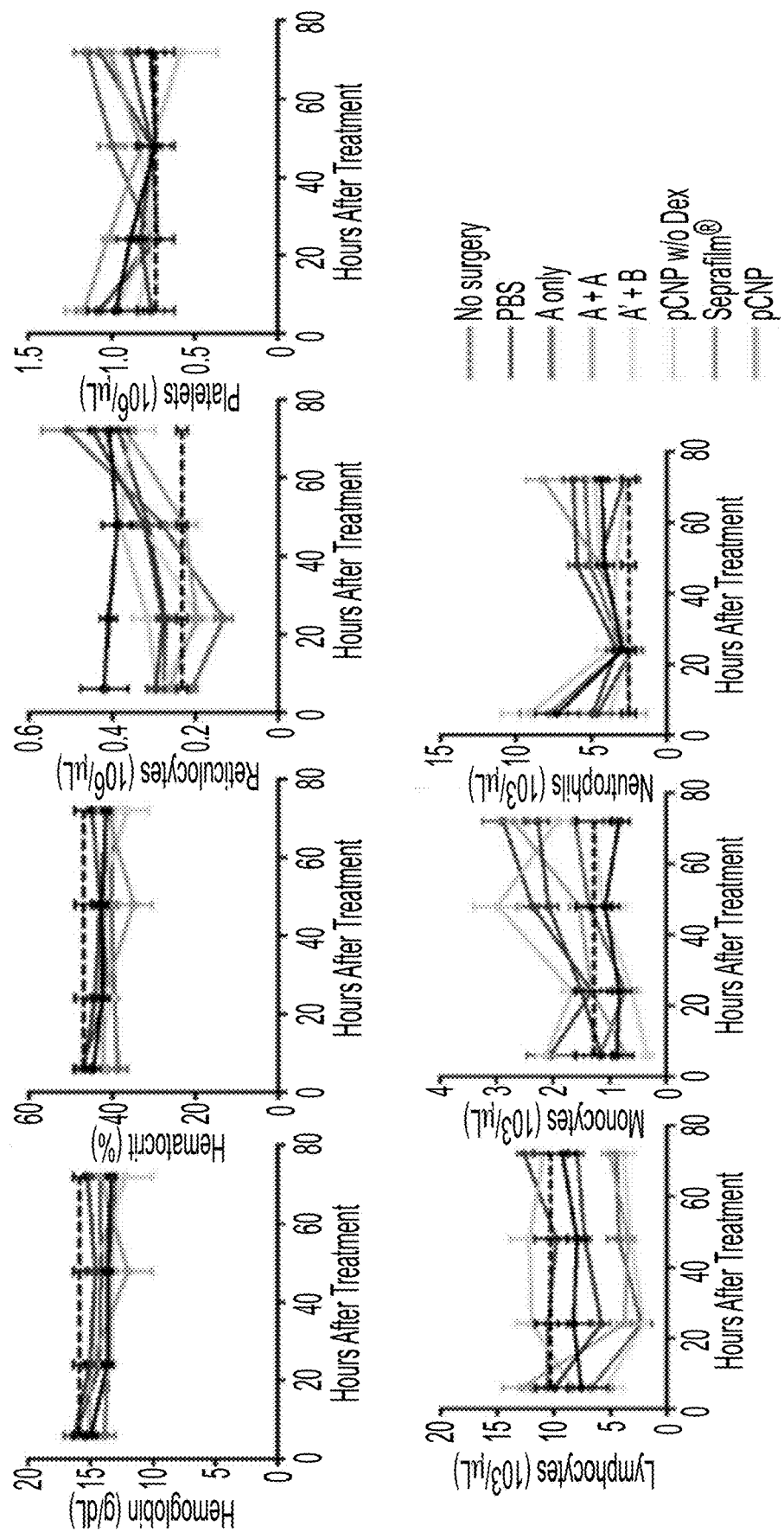
FIG. 16 shows whole blood assessment of rats at 6 h, 24 h, 48 h and 72 h after treatments. a, Hemoglobin count. b, Hematocrit count. c, Reticulocyte count. d, Platelet count. e, Lymphocyte count. f, Monocyte count. g, Neutrophil count. Data represents mean±standard error of the mean (SEM). (For A+A, n=6; For pCNP w/o Dex, n=7; For Seprafilm®, n=8; For other groups, n=9).
Figure 17A:
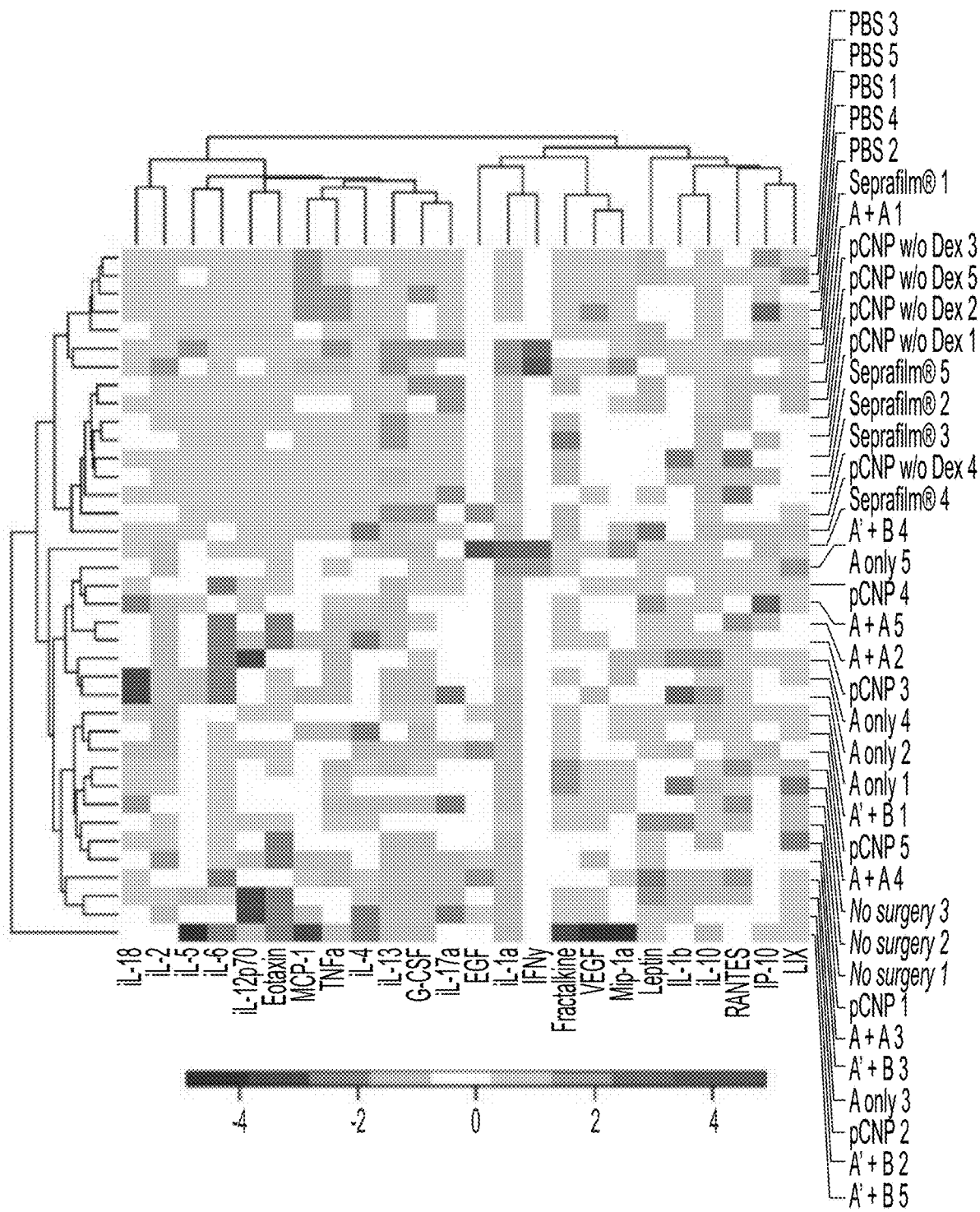
FIG. 17 shows how pCNP reduces inflammatory cytokines/chemokines in serum in a parietal peritoneal excision (PPE) model in rats. (a, b) Heatmap showing serum cytokine/chemokine levels in each sample across all treatment groups after 24 h (a) and 72 h (b). Samples (y axis) and cytokine/chemokine levels (x axis) were heterarchical clustered. Color scale reflects cytokine/chemokine expression magnitude (red: high, blue: low).
Figure 17B:
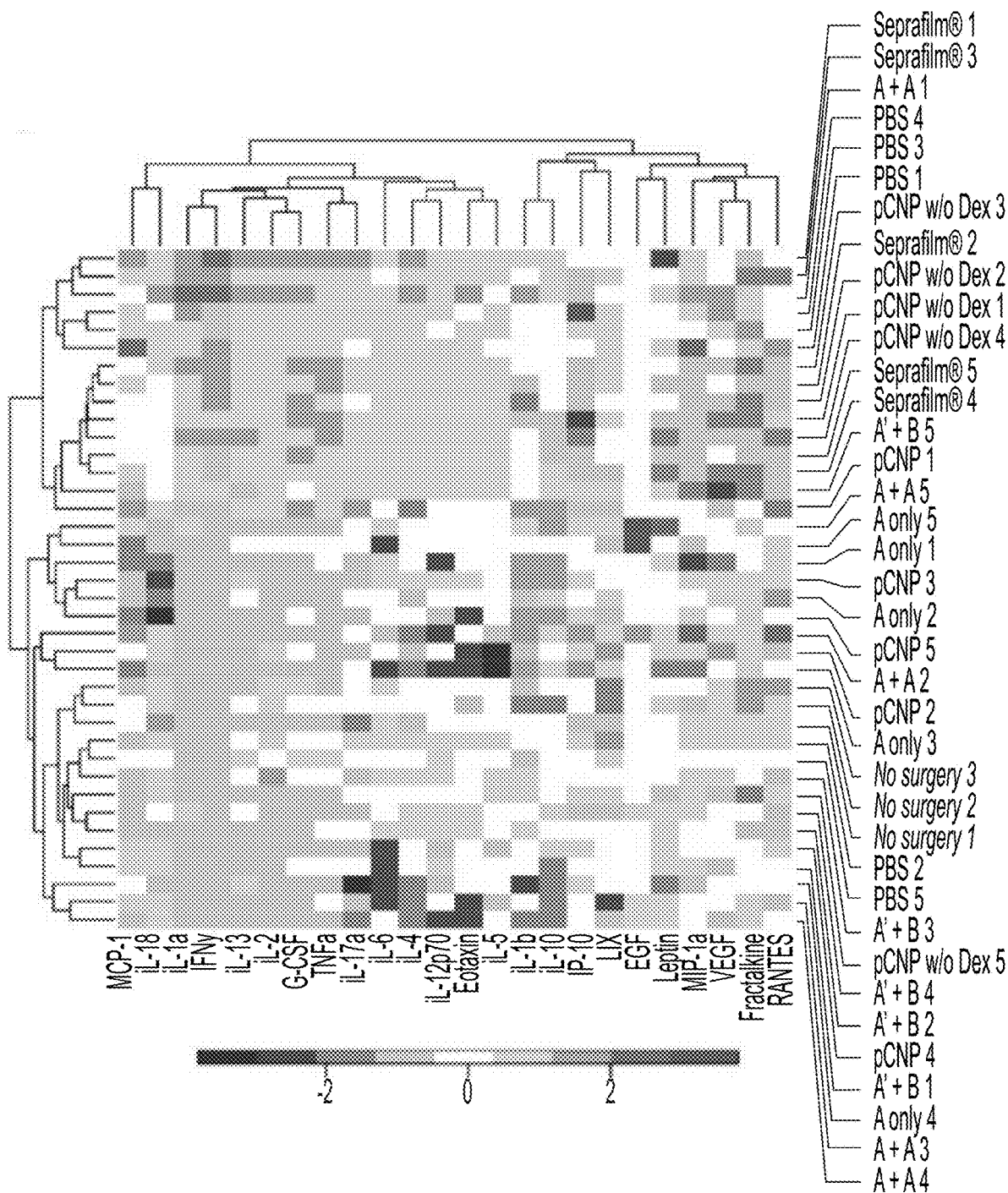
Figure 18A:
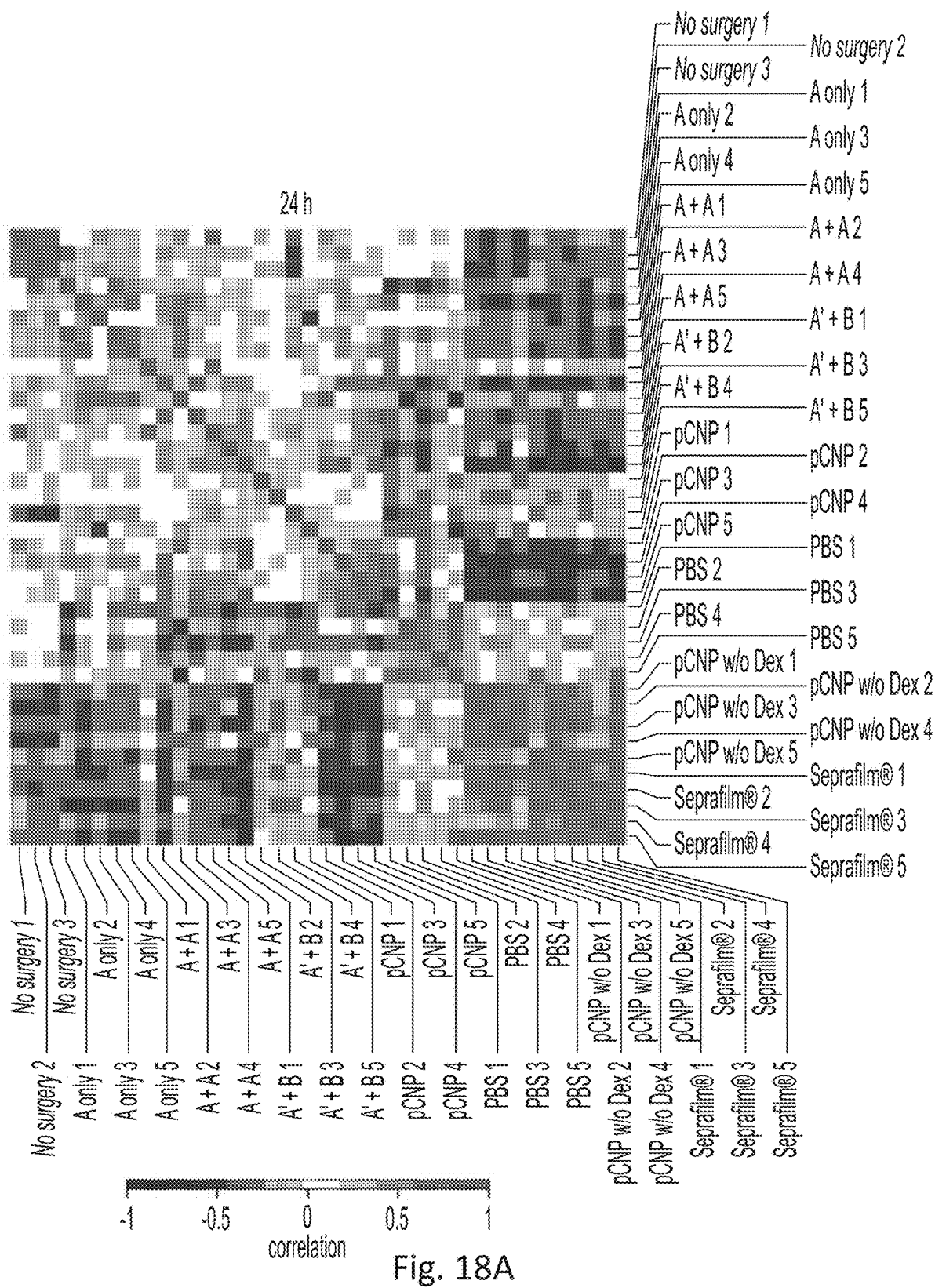
FIG. 18 shows a Pearson correlation matrix of each sample versus other samples (including itself as the diagonal line). The matrix demonstrates similarities of inflammation among different treatment groups.
Figure 18B:
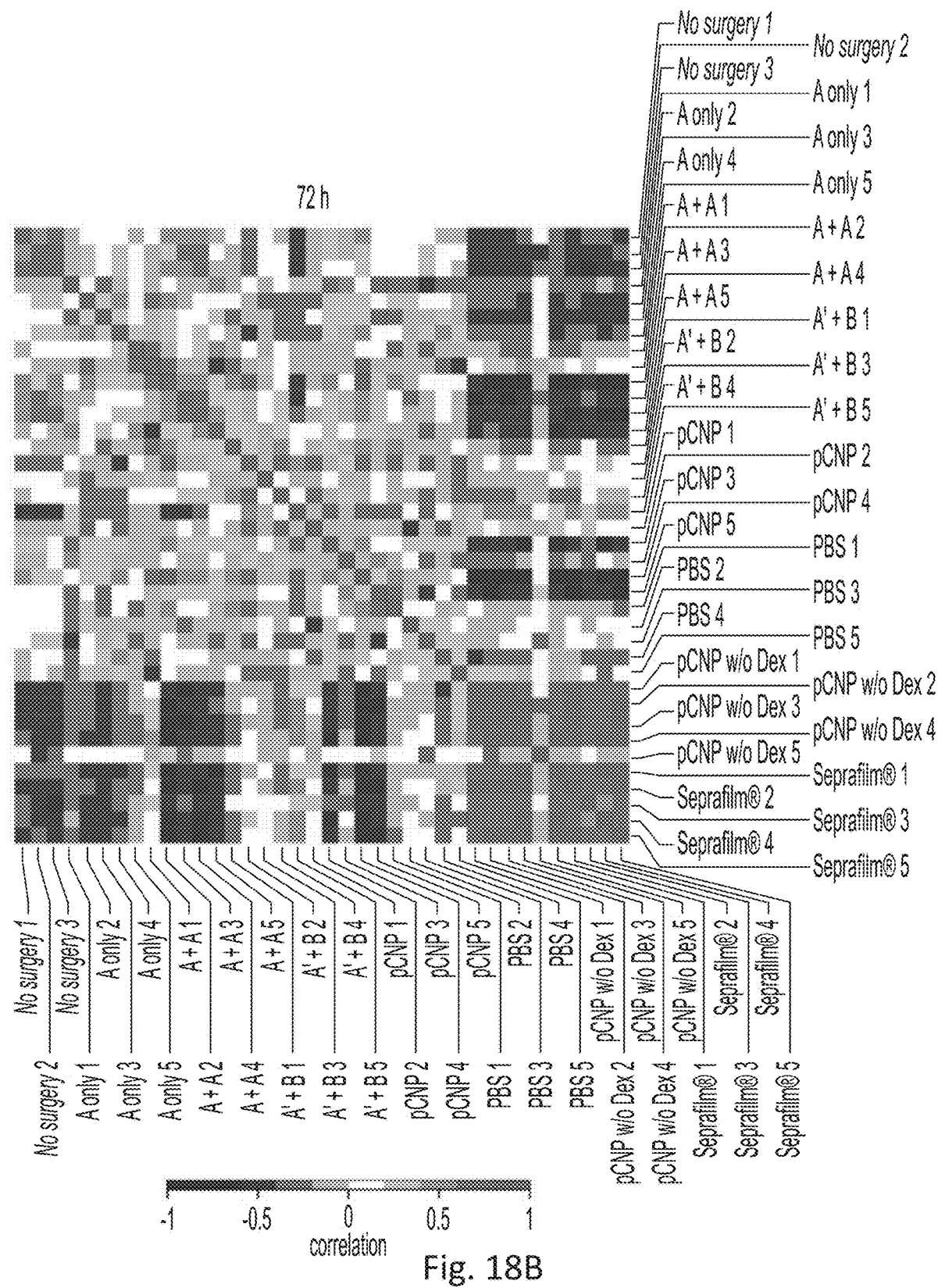
Figure 19:
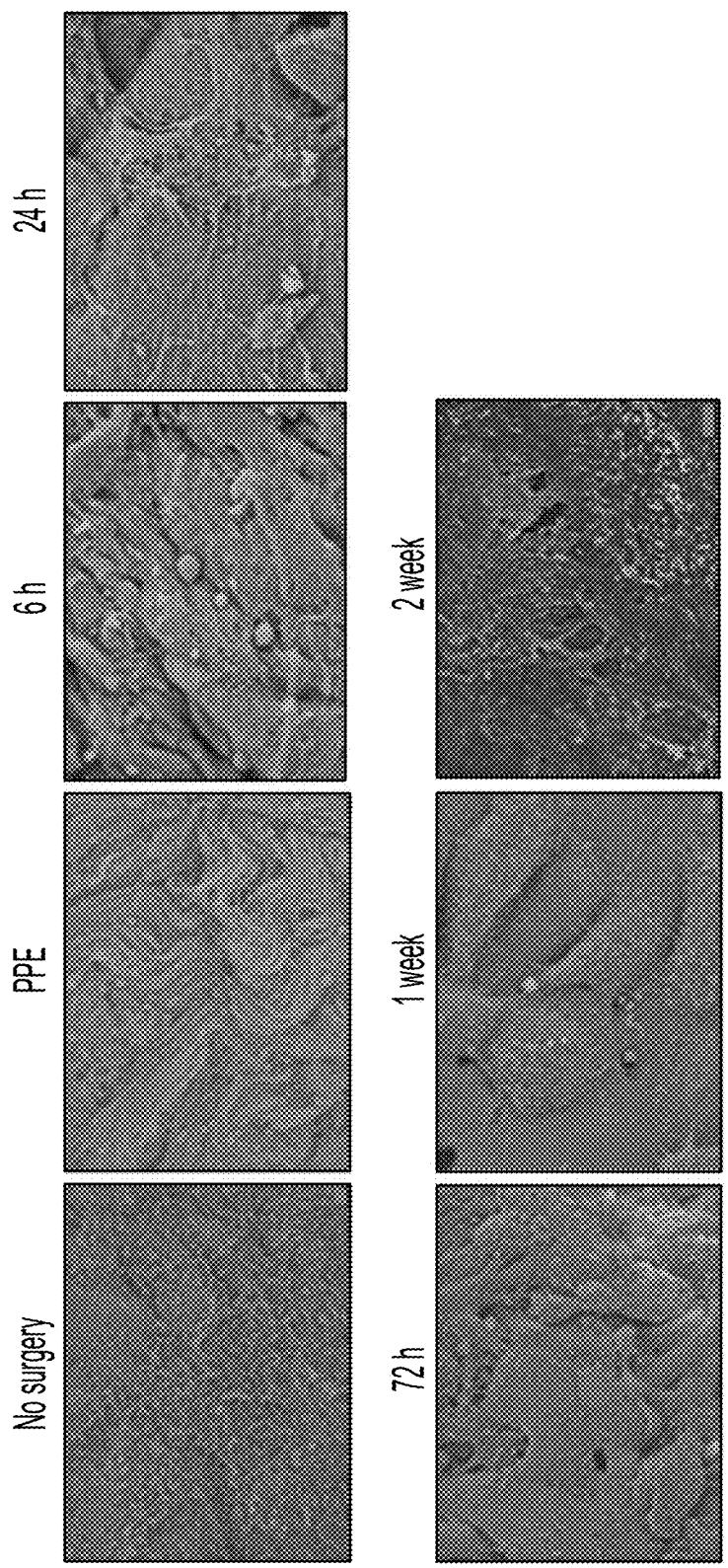
FIG. 19 depicts FESEM images showing the healing process of rats' abdominal wall after PPE surgery and subsequent treatment with pCNP.
Figure 20:
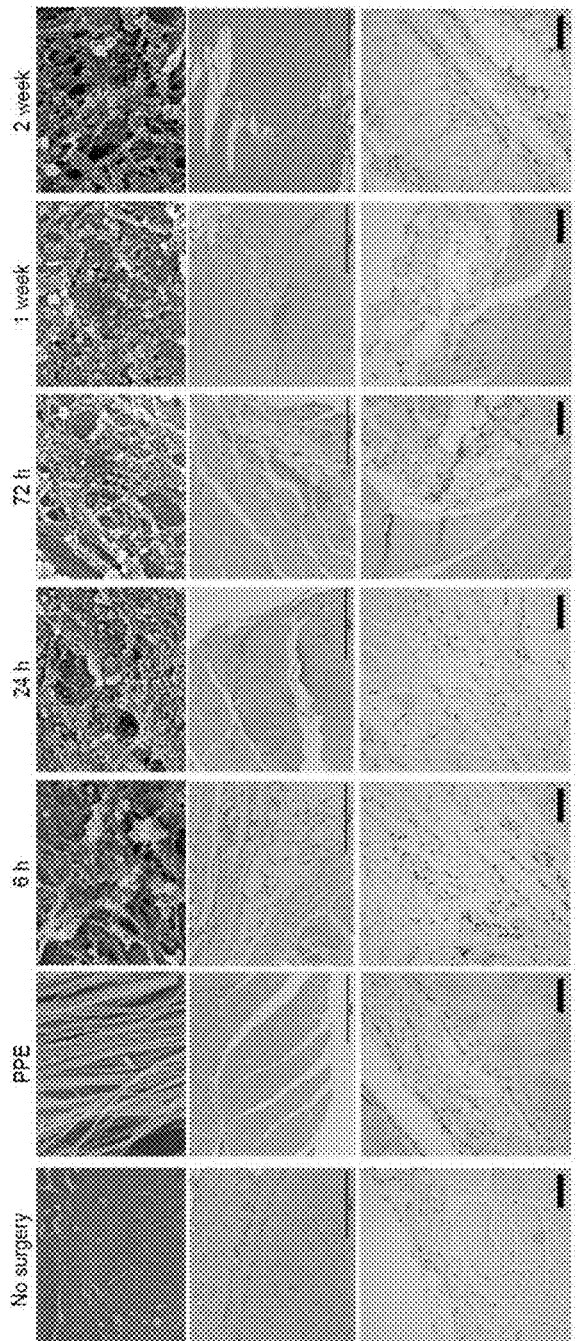
FIG. 20A-FIG. 20C shows how pCNP retains on collagen fibers and reduces local inflammation during a postsurgical healing process in a parietal peritoneal excision (PPE) model in rats.
Figure 21:
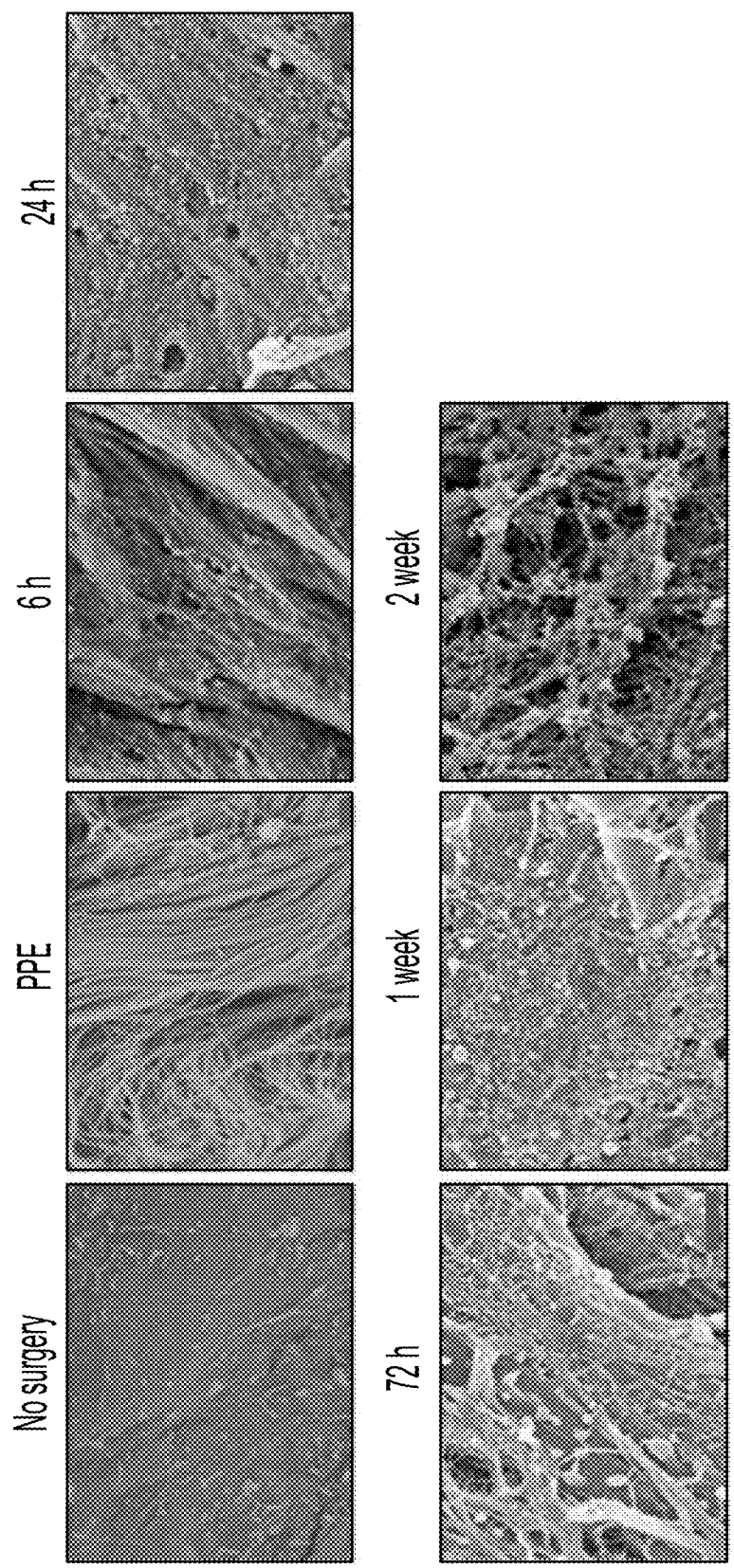
FIG. 21 depicts zoomed out FESEM images showing the retention and biodegradation of pCNP on rats' abdominal wall at 6 h, 24 h, 72 h, 1 week and 2 weeks after surgery and subsequent treatment with pCNP. Scale bar=1 µm.
Figure 22:
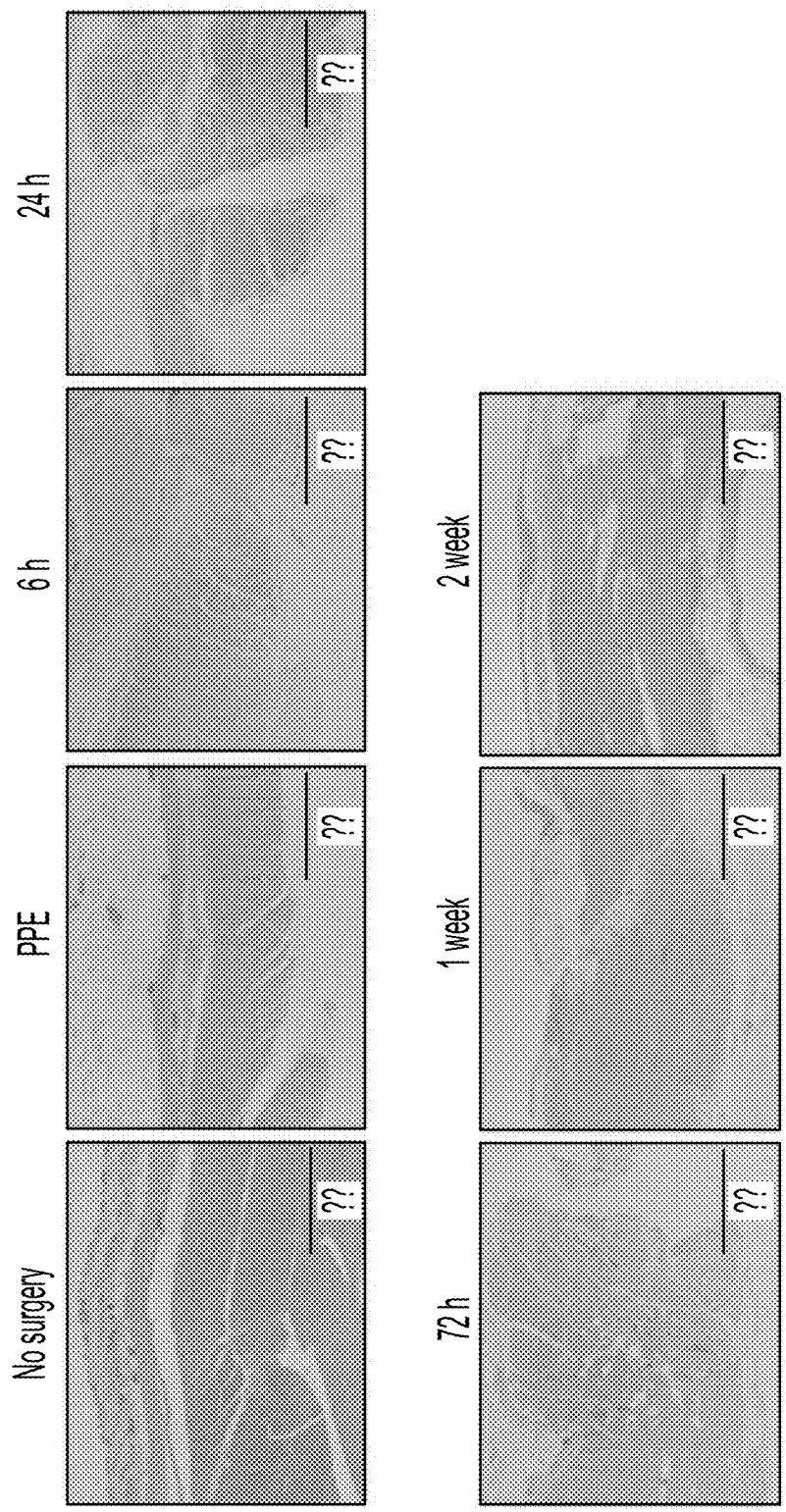
FIG. 22 shows zoomed out hematoxylin and eosin (H&E) staining images on rats' abdominal wall at 6 h, 24 h, 72 h, 1 week and 2 weeks after surgery and subsequent treatment with pCNP. Scale bar=1 mm.
Figure 23:
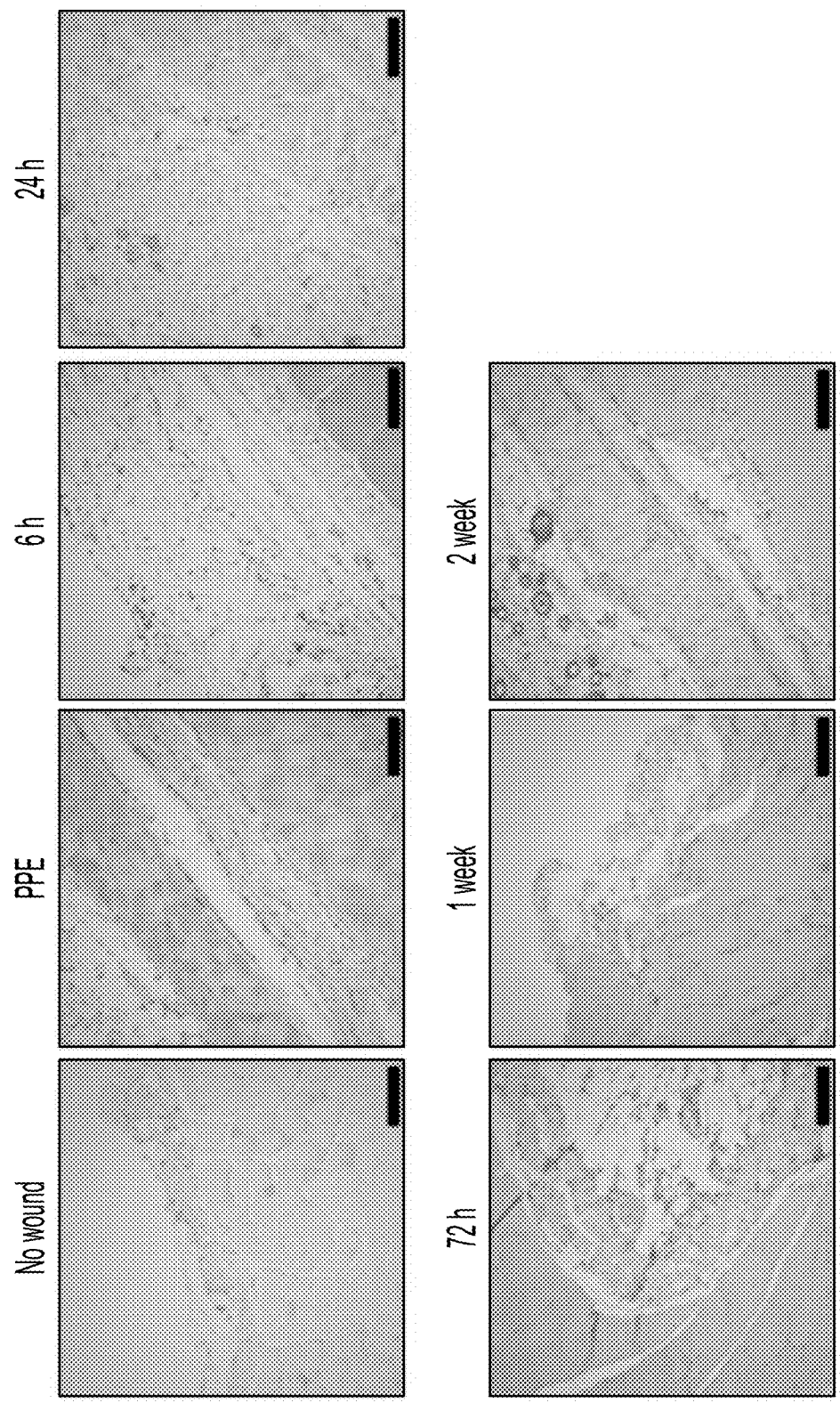
FIG. 23 shows zoomed out CD45 immunohistochemistry (IHC) staining images of rats' abdominal wall at 6 h, 24 h, 72 h, 1 week and 2 weeks after surgery and subsequent treatment with pCNP. Scale bar=200 µm.
Figure 24A:
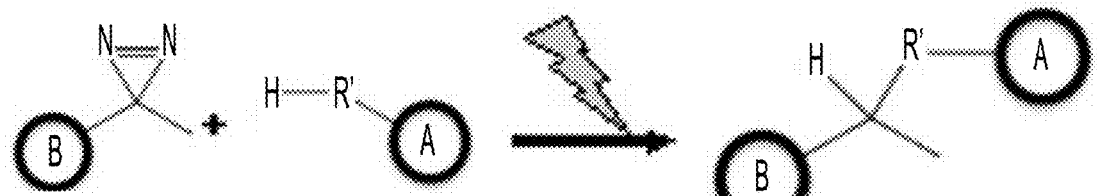
FIG. 24 shows a series of different chemical mechanisms for particle crosslinking.
Figure 24B:
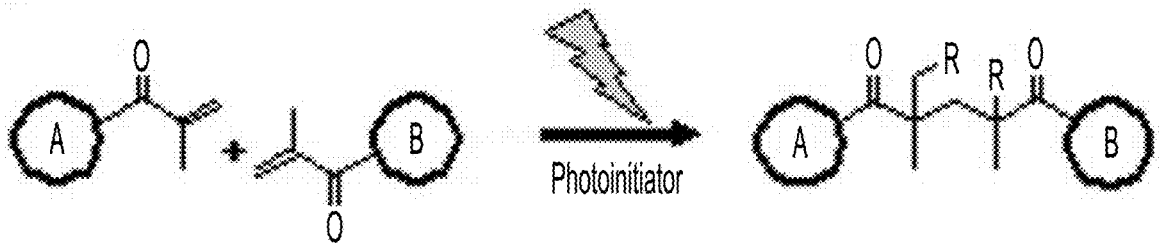
Figure 24C:
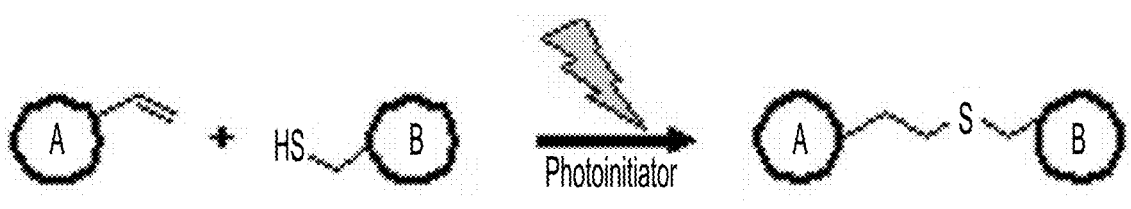
Figure 24D:
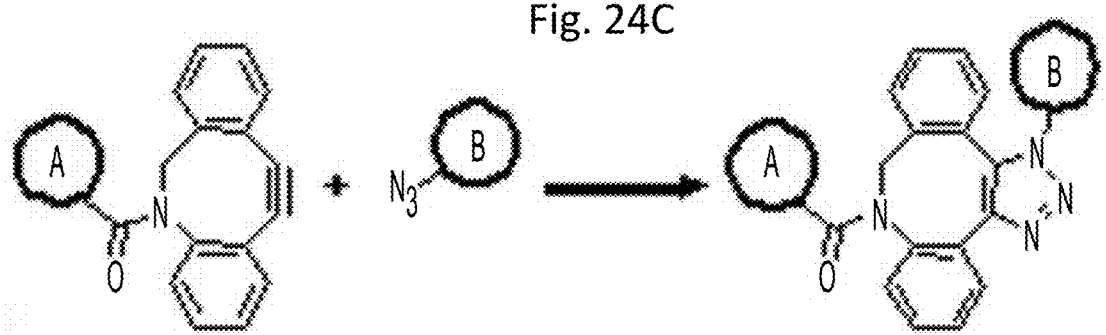
Figure 24E:
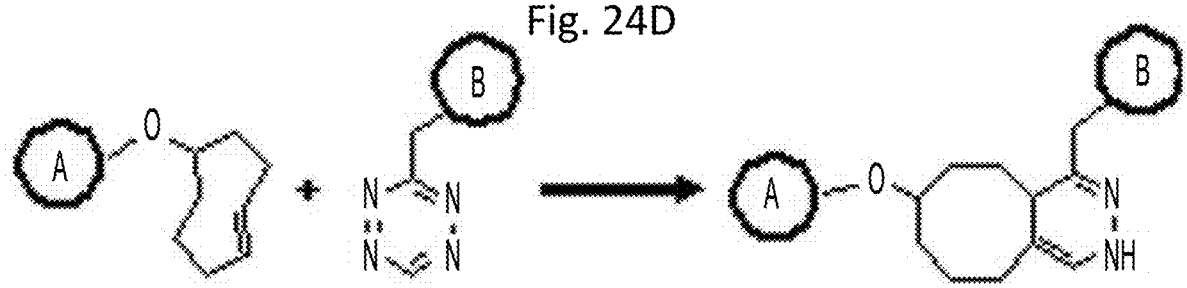

We assessed potential systemic adverse events in the rats. Potential side effects include anemia, high WBC from systemic exposure of dexamethasone, bleeding, or infection. Complete blood counts (CBC) were obtained in the animals after PPE surgery. (FIGS. 15a and b, FIG. 16). The red blood cell count (RBC), hemoglobin (HGB), hematocrit (HCT) and platelets were all within normal ranges after surgery in the experimental arms. An increase of reticulocytes indicated the loss of blood during surgery and RBC recovery after surgery. A decrease of white blood count (WBC) was detected at 24 h, but returned to a normal range after 72 h. A limited decrease of lymphocyte, and increase of neutrophil and monocyte were observed after surgery, consistent with postsurgical reactions. All rats remained alive through the 14 days between the procedure and the second-look laparotomy with no obvious deterioration of physical symptoms, indicating pCNP was safe in rats. Another potential side effect for Dex-Pal is increase in blood glucose. We monitored the level of blood glucose in the rats at 6 h, 24 h, 48 h and 72 h post surgery (FIG. 15C). An initial increase was observed for all treatment groups at 6 h after surgery, likely due to stress and glucocorticoid release in response to stress. From then on, the blood glucose decreased and reached normal levels at 72 h after surgery.

pCNP Reduces Inflammatory Cytokines/Chemokines in Serum in Parietal Peritoneal Excision (PPE) Model in Rats As inflammatory level plays an important role in adhesion formation, we assessed cytokines/chemokines in serum 24 h and 72 h post-surgery with different treatments using immunology multiplex assay (FIG. 17, FIG. 18). Hierarchical clustering showed that PBS, pCNP w/o Dex and Seprafilm® groups clustered together and showed high expression of inflammatory markers such as interleukin family, TNFα, IFNγ, G-CSF and MCP-1. On the contrary, pCNP group showed similar inflammatory level to no surgery group, suggesting a decreased level of inflammation during postsurgical healing process prevented adhesion formation.

pCNP Retains on Collagen Fibers and Reduces Local Inflammation During Postsurgical Healing Process in Parietal Peritoneal Excision (PPE) Model in Rats To further understand the functions of pCNP during the healing process, we treated rats bearing PPE with pCNP and acquired their injured abdominal wall after 6 h, 24 h, 72 h, 1 week and 2 weeks. FESEM images showed that collagen fibers were exposed in PPE model and the injured surface was recovered after 2 weeks (FIG. 19). By magnifying the surface, we observed a dense NP layer formed and retained on collagen fibers for the whole process (FIG. 20A, FIG. 21). We also found a decrease in NP density after 2 weeks, indicating the biodegradation of pCNP. Hematoxylin and eosin (H&E) staining showed that mild inflammation occurred at 6 h mainly due to the surgery, and no severe active inflammation (immune infiltrate) in other experimental arms (FIG. 20B, FIG. 21). The local inflammatory degree was further confirmed by CD45 immunohistochemistry (IHC), which consisted with H&E staining results (FIG. 20C, FIG. 23). This suggests that pCNP was biocompatible and did not cause any severe inflammation in the tissue where they are administered.

DISCUSSION

A challenge in this study relates to the fact that adhesion formation is both qualitative and quantitative. To fully capture both measures of adhesions, we utilized a well-established adhesion scoring system to analyze our in vivo data. To avoid bias, we blinded the surgeons during this experiment. Moreover, we have included the raw images herein to enable unbiased interpretation.

We also want to note that pCNP is shown to be safe in our studies. Given the materials for pCNP are Generally Regarded as Safe (GRAS) materials, we believe this technology is readily translated into clinical practice.

In summary, we report the first biologically targeted approach to prevent postsurgical adhesions. We combined a collagen IV targeted NP with a photo-crosslinkable NP to form a dense barrier over injured epithelial/mesothelial surfaces in a biologically targeted fashion. The barrier (pCNP) is also capable of delivering anti-inflammatory therapeutics to further prevent adhesion formation. Our study also demonstrates the potential applications of biologically targeted nanomaterials.

Materials and Methods

Materials

Methoxy-poly(ethylene glycol)-poly(lactic-co-glycolic acid) block copolymer (mPEG-PLGA) (AK029; LA:GA=50:50 (w:w); MW: ~3000:36,000 Da), poly(lactic-co-glycolic acid)-poly(ethylene glycol)-maleimide block copolymer (PLGA-PEG-Mal) (AI110; MW: ~30,000-5,000 Da), poly(lactic-co-glycolic acid)-poly(ethylene glycol)-carboxylic acid block copolymer (PLGA-PEG-COOH) (AI034; MW: ~3,400:17,000 Da) were obtained from Polyscitech®. Collagen IV-targeting peptide with an amino acid sequence of KLWVLPKGGGC (SEQ ID NO: 1) was purchased from UNC High-Throughput Peptide Synthesis and Array Facility. The peptide was synthesized via automated Fmoc solid phase peptide synthesis method and purified by high-performance liquid chromatography (HPLC). Peptide homogeneity was confirmed by MALDI-TOF mass spectroscopy and analytical HPLC. Dexamethasone 21-Palmitate was obtained from Toronto Research Chemicals. Polyethyleneimine (M.N. 60,000, 50 wt. % aq. solution, branched), acetone, dimethylformamide (DMF) anhydrous, methanol (MeOH), water (HPLC grade) were obtained from Fisher Scientific. Sulfosuccinimidyl 6-(4,4'-azipentanamido) hexanoate (sulfo-LC-SDA), EDC/sulfo-NHS, triethylamine, were obtained from Sigma-Aldrich. Seprafilm® was obtained from Sanofi Biosurgery.

pCNP Preparation pCNP was prepared separately. NP-A was fabricated through nanoprecipitation technique (28, 29). Collagen IV-targeting peptide-functionalized poly(ethylene glycol)-poly (lactic-co-glycolic acid) (Col-PEG-PLGA) was synthesized first according to previous reports. Briefly, maleimide functionalized PEG-PLGA (Mal-PEG-PLGA) and collagen IV targeting peptide (KLWVLPKGGGC-NH2) (SEQ ID NO: 1) were dissolved in 5 mL anhydrous DMF with a molar ratio of 1:1.2. Triethylamine (5 µL) was added and the reaction was stirred under nitrogen at room temperature for 24 h. The solution was precipitated in cold MeOH and was centrifuged at 3,000 g for 10 minutes. The pellet was washed with MeOH twice and dried under vacuum. To prepare NP-A, Col-PEG-PLGA and PEG-PLGA (1:4 weight ratio) were dissolved into acetone with a final polymer concentration of 10 mg/mL. Dex-Pal (5% wt of total polymer) was added into the solution. The organic phase was added dropwise into aqueous phase (endotoxin free $H_2O$) through a syringe under the oil to water ratio of 1:2. The solution was stirred at room temperature under a vacuum until the acetone completely evaporated. The solution were centrifuged and washed with endotoxin free $H_2O$. To prepare NP—B, NP—COOH was first prepared through a similar nanoprecipitation technique by using COOH-PEG-PLGA and PEG-PLGA (1:1 weight ratio). The NP—COOH (1 mg/mL) were reacted with EDC/sulfo-NHS in PBS for 10 minutes, followed by adding branched PEI with a concentration of 2 mg/mL for a final NP to PEI weight ratio of 5:4. Nanoparticles with PEI layer (NP-PEI) was then washed twice and collected. Next, NP-PEI was stirred with sulfo-LC-SDA (3:1 by weight) in PBS for half an hour at room temperature. The nanoparticles were finally harvested after washing twice with endotoxin free $H_2O$.

pCNP Characterization pCNP was characterized by intensity-average diameter ($D_h$, also known as hydrodynamic diameter) and mean zeta potential (mean $\zeta$) using Zetasizer Nano ZS Instrument (Malvern, Inc.). All measurements were based on the average of three separate measurements.

The drug loading of Dex-Pal in NP-A (weight of Dex-Pal divided by weight of NP-A) was tested by HPLC. A known amount of freeze-dried NP-A was dissolved in 1 mL DCM. After evaporating the DCM, 1 mL of 50% acetonitrile (ACN) in water was added to dissolve the extracted drugs. The solution was then filtered by 0.45 mm PVDF membrane for HPLC analysis. The column effluent was detected at 236 nm with a continuous gradient mobile phase from 50% to 100% ACN in water over 20 minutes. All values were based on the average of three separate replicate measurements.

In Vitro Analysis for pCNP

A collagen IV-coated glass cover was prepared for in vitro analysis by incubating a Poly-D-Lysine (PDL) coated glass cover slip (Neuvitro, GG-12-1.5-PDL) in a 100 µg/mL solution of collagen IV overnight at room temperature. The collagen IV-coated glass cover was washed twice before use.

10 mg/mL NP with (NP-A) or without (NP-A') collagen IV-targeting ligand was incubated with collagen IV-coated or non-coated glass covers for 10 minutes at room temperature. The glass covers were then washed twice with saline and water. Next, 10 mg/mL NP-B was incubated with the glass covers for 10 minutes under UV irradiation at 365 nm and 50 mW/cm². Then, the glass covers were washed with saline and water, and left to air dry at room temperature. The NP layer formation was checked by Zeiss Supra 25 field emission scanning electron microscope (FESEM).

For in vitro drug release profile, pCNP was first formed on collagen IV-coated glass covers as it mentioned above. The glass covers were placed in PBS with or without esterase (*T. lanuginosus* lipase, Sigma) at 100 U/mL and shaken at 37° C. The release buffer was substituted at 6 h, 24 h, 48 h, 72 h, 120 h, 9 days and 14 days and freeze-dried for quantitative analysis. Cumulative release of Dex-Pal and its active form dexamethasone were performed with a Shimadzu SPD-M20A high performance liquid chromatography (HPLC) equipped with a diode array detector and a C18 25 cm*4.6 mm, 5 μm column (Supelco, Sigma). Samples were eluted using a gradient binary solvent system from 50% acetonitrile in water to 100% for Dex-Pal and 10%-80% for dexamethasone at a flow rate of 1 mL/min. Dex-Pal and dexamethasone elution were monitored at 236 nm and 240 nm, respectively. The experiment was repeated three times.

For in vitro cytotoxicity analysis, 96-well plate was coated with collagen IV and seeded with NIH/3T3 murine fibroblast cells at 10,000/well for 2 h and 24 h, 5,000/well for 72 h. NP-A with or without Dex-Pal was incubated for 10 min and washed twice with saline. NP-B was incubated for 10 min with or without UV irradiation at 365 nm and 50 mW/cm$^2$. The plate was then washed twice with saline and added cell culture medium at 100 μL/well. Different NP concentrations at 5 mg/mL, 10 mg/mL and 20 mg/mL were used for both NP-A and NP-B. After 2 h, 24 h and 72 h, the plate was tested with MTS assay (CellTiter 96® AQueous One Solution Cell Proliferation Assay, Promega).

Photo-DSC Analysis

Cross-linking kinetics were determined by photocalorimetry using a Discover DSC with the PCA accessory, equipped with a Omnicure S-2000 mercury UV light source with a 365 nm external filter (TA instruments, New Castle, DE). 20 μL of the nanoparticle solution was added to an aluminum DSC sample pan without a lid and placed in the DSC cell, which was held at a constant temperature of 5° C. under a 10 mL/min nitrogen flow. After a 2.5 minutes isothermal step, samples were exposed to UV light for 20 minutes at 50 mW cm$^{-2}$. Enthalpy was calculated by integrating the normalized heat flow curve using a horizontal baseline at the heat flow value after 20 minutes of exposure.

Sample Size Calculations and Analysis for In Vivo Efficacy Studies

Sample size is calculated based on our preliminary data. We calculated an effect size of 1.821. The nonparametric analog of this effect size can be stated in terms of p1=Pr (X<Y), or an observation in Group X is less than an observation in Group Y when H1 is true. The null hypothesis being tested is p1=0.5. For effect size 1.821, p1=0.099. A sample size of 8 in each group will have 80% power to detect a probability of 0.099 that an observation in Group X is less than an observation in Group Y, using a Wilcoxon (Mann-Whitney) rank-sum test, with a 0.05 two-sided significance level.

Animal Model

The in vivo analysis utilized parietal peritoneum excision (PPE) to generate adhesion on rat (FIG. 8). Briefly, a survival-surgery was carried out on Sprague Dawley rats in which a ~2×5 cm patch of peritoneum and the underlying muscle layer was excised from the left abdominal wall remote from the midline laparotomy. The wound was washed with saline and closed. After 14 days, a second-look laparotomy was performed to assess adhesion formation according to the scoring systems described in literature. Briefly, a four-point scale was performed for qualitative assessment of adhesion where 0=no adhesions; 1=filmy adhesions; 2=moderate-thickness adhesion; 3=dense-thickness adhesion. A five-point scale was performed for quantitative assessment of adhesion where the percentage of adhesion area to the surgical area was quantified as 0=0% adhesions; 1=less than 25%; 2=25%-49%; 3=50%-74%; 4=75%-100% adhesions.

Treatment of Injured Surface with pCNP on Rats

Sprague Dawley rats at 25-45 weeks of age and 400-600 g of body weight underwent the aforementioned survival surgery. Prior to closure, rats were laid on the side ipsilateral to the excision to form a pocket-like cavity for NP incubation (FIG. 10A and FIG. 10B). NP-A (2 mL) at 10 mg/mL was first administered to the peritoneal cavity and allowed to incubate for 10 minutes. The injured surface was washed with saline twice. NP-B (2 mL) at 10 mg/mL was then administered to the peritoneal cavity and the injured site was concurrently irradiated for 10 minutes with 365 nm UV light at an intensity of 50 mW cm' from light guides, which were fitted to an Omnicure S-2000 light source as used in the photo-DSC apparatus. The peritoneal cavity was washed twice with saline after incubation and the wound was closed. The rats were under constant monitoring and blood was collected at 6 h, 24 h, 48 h and 72 h after surgery for analysis. 100 μL whole blood was collected for complete blood count (CBC) test and 20 μL serum was collected for blood glucose test. After 14 days, rats were euthanized by $CO_2$. The abdomen was opened via a right lateral U-shaped laparotomy to prevent the disturbance of adhesion area. The lateral with treatment and the other lateral without any manipulation were recorded by optical photos. Two experimenters, blinded to the procedure, assessed all the adhesions according to the aforementioned scoring systems. The related tissues including muscle, skin and peritoneal adhesion were excised and fixed in 10% neutral buffered formalin for histological analysis.

Histological Analysis

Tissues were fixed in 10% neutral buffered formalin at room temperature for approximately 3 days. Fixed tissues were processed on a Leica ASP 6025 tissue processor, embedded in paraffin wax, and sectioned at 4 μm thickness on a Leica RM2245 microtome and mounted on VWR Superfrost Plus microscope slides. Tissue sections were H&E stained using Richard-Allen Hematoxylin 2 and Eosin Y and cover-slipped. Histologic changes were evaluated by a board-certified veterinary pathologist.

Immunohistochemical Analysis

Immunohistochemical analysis was performed on paraffin slides using anti-collagen I antibody (34710, Abcam), anti-collagen IV antibody (6586, Abcam), anti-fibronectin antibody (23751, Abcam) and anti-CD45 antibody (10558, Abcam). Antigen retrieval was performed using Ventana's CC2 (pH 6.0) for 8 minutes at 90° C. for anti-collagen I; Ventana's CC2 (pH 6.0) for 40 minutes at 100° C. for anti-collagen IV; Ventana's CC1 (pH 8.5) for 8 minutes at 90° C. for anti-fibronectin; Ventana's CC2 (pH 6.0) for 40 minutes at 90° C. for anti-CD45. The slides were given a hydrogen peroxide block for 32 minutes and then incubated in a blocking reagent (Rodent Block R, RBR962G, Biocare) for 1 h at room temperature. The primary antibody was added at 1:100 for anti-collagen I and 1:50 for the others using Discovery Ab Diluent, 760-108, followed by the secondary antibody (Ventana Omap OmniMap anti-Rb-HRP, 760-4311, Ready to Use) for 32 minutes at room temperature. The slides were then treated with DAB and counterstained with Hematoxylin II for 12 minutes and then Bluing Reagent for 4 minutes.

Time-Point Tissue Analysis

Rats bearing PPE surgery were treated by pCNP. The injured tissues were taken after 6 h, 24 h, 72 h, 1 week and 2 weeks of the treatment, rinsed briefly with PBS to remove surface debris, followed by immersion fixation in 10% neutral buffered formalin for histological analysis, immunohistochemical analysis and FESEM. To prepare FESEM samples, after initial fixation for several hours to overnight in formalin, the region of interest was dissected out and placed in 2% paraformaldehyde/2.5% glutaraldehyde/0.15M sodium phosphate buffer, pH 7.4. Specimens were stored in the fixative overnight to several days at 4° C. before processing for SEM. After three washes with 0.15M sodium phosphate buffer, pH 7.4 (PB), the samples were post-fixed in 1% osmium tetroxide in PB for one hour followed by three 30 minute washes in deionized water. The samples were dehydrated in a grade series of ethanol, transferred to a Samdri-795 critical point dryer and dried using carbon dioxide as the transitional solvent (Tousimis Research Corporation, Rockville, MD). Tissues were mounted on aluminum planchets using silver paste and coated with 15 nm of gold-palladium alloy (60Au:40Pd, Hummer X Sputter Coater, Anatech USA, Union City, CA). Images were taken using a Zeiss Supra 25 FESEM operating at 5 kV, using the SE2 detector, 30 µm aperture, and approximate working distance of 10 to 12 mm (Carl Zeiss Microscopy, LLC, Peabody, MA).

Analysis of Post-Surgery Inflammatory Levels

Rats bearing PPE surgery were treated with different experimental arms. Serum was collected at 24 h and 72 h after surgery with SST™ Serum Separation Tubes (BD Vacutainer™ Venous Blood Collection Tubes). Immunology multiplex assay was performed with milliplex map rat cytokine/chemokine magnetic bead panel (RECYMAG65K27PMX, Millipore). To examine and visualize inflammatory levels after different treatments, each cytokine/chemokine level was log 2 transformed and standardized. Hierarchical clustering with Euclidean distance and complete linkage was performed and heatmap was used for visualization. Pearson correlations among samples were also calculated and plotted. All clustering and heatmap analysis were done under R version 3.5.1 using package gplots (heatmap.2).

Statistics

Unpaired, 2-tailed Student t test or Mann Whitney test was used for comparison of experimental groups. Differences were considered to be significant for *P<0.05, P<0.01, *P<0.001, ****P<0.0001. Prism software was used for data analysis and to prepare graphs (GraphPad, version 6.0c). Data represent mean±SEM. Hierarchical clustering with Euclidean distance and complete linkage was performed. Pearson correlations among samples were calculated and plotted. All clustering and heatmap analysis were done under R version 3.5.1 using package gplots (heatmap.2).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

Citation or identification of any reference in this application is not an admission that such reference is available as prior art.

Efforts have been made to ensure accuracy with respect to numbers used (e.g. amounts, temperature, etc.) but some experimental errors and deviations should be accounted for.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller ranges is also encompassed, subject to any specifically excluded limit in the stated range. Where the stated range includes one or both of the limits, ranges excluding either or both of those included limits are also included.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

The disclosures of all cited references including publications, patents, and patent applications are expressly incorporated herein by reference in their entirety.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation. One skilled in the art will recognize many methods and materials similar or equivalent to those described herein, which could be used in the practicing the subject matter described herein. The present disclosure is in no way limited to just the methods and materials described.

The invention claimed is:

1. A method of treating a surgical site comprising:
contacting the surgical site with a particle formulation comprising targeting particles and scaffolding particles; wherein the targeting particles comprise poly(ethylene glycol)-poly(lactic-co-glycolic acid) copolymer and a collagen IV-targeting peptide; and the scaffolding particles comprise:
a core comprising poly(ethylene glycol)-poly(lactic-co-glycolic acid) copolymer; and
a shell, wherein the surface of the scaffolding particles comprise at least one diazirine group; and
UV-induced crosslinking the targeting particles and scaffolding particles to provide a composite membrane at the surgical site, wherein formation of post-surgical adhesions are inhibited by the composite membrane.

2. The method of claim 1, wherein the targeting particles further comprise one or more pharmaceutical compositions, and wherein the method further comprises releasing the one or more pharmaceutical compositions from the composite membrane.

3. The method of claim 2, wherein said one or more pharmaceutical compositions is selected from the group consisting of dexamethasone, dexamethasone 21-Palmitate, and a combination thereof.

4. The method of claim 2, wherein greater than 10 percent of the one or more pharmaceutical compositions is released within 24 hours of membrane formation.

5. The method of claim 2, wherein the one or more pharmaceutical compositions is released over a time period of at least 14 days.

6. The method of claim 1, wherein the surgical site comprises peritoneal surfaces.

7. A method of treating a surgical site comprising:
contacting the surgical site with a particle formulation comprising scaffolding particles and carrier particles transporting one or more pharmaceutical compositions; wherein the carrier particles comprise poly(ethylene glycol)-poly(lactic-co-glycolic acid) copolymer and a collagen IV-targeting peptide; and the scaffolding particles comprise:
a core comprising poly(ethylene glycol)-poly(lactic-co-glycolic acid) copolymer; and
a shell, wherein the surface of the scaffolding particles comprise at least one diazirine group; and
UV-induced crosslinking the carrier particles and scaffolding particles to provide a composite membrane at the surgical site, wherein formation of post-surgical adhesions are inhibited by the composite membrane.

8. The method of claim 7, wherein the one or more pharmaceutical compositions inhibit tissue inflammation.

9. The method of claim 8, wherein said one or more pharmaceutical compositions is selected from the group consisting of dexamethasone, dexamethasone 21-Palmitate, and a combination thereof.

10. The method of claim 7, further comprising releasing the one or more pharmaceutical compositions from the composite membrane.

11. The method of claim 10, wherein the one or more pharmaceutical compositions is released over a time period of at least 14 days.

12. The method of claim 7, wherein the carrier particles comprise one or more chemical moieties targeting one or more biomolecular species located at the surgical site.

13. The method of claim 7, wherein the surgical site comprises peritoneal surfaces.

14. A kit comprising:
(i) a vial containing a first particle formulation comprising targeting particles; and
(ii) a vial containing a second particle formulation comprising scaffolding particles; or
(i) a vial containing a first particle formulation comprising carrier particles; and
(ii) a vial containing a second particle formulation comprising scaffolding particles;
wherein the carrier particles and targeting particles comprise poly(ethylene glycol)-poly(lactic-co-glycolic acid) copolymer and a collagen IV-targeting peptide; and the scaffolding particles comprise:
a core comprising poly(ethylene glycol)-poly(lactic-co-glycolic acid) copolymer; and
a shell, wherein the surface of the scaffolding particles comprise at least one diazirine group.

15. A composite membrane formed by:
crosslinking a first particle composition comprising targeting particles with a second particle composition comprising scaffolding particles;
or, crosslinking a first particle composition comprising carrier particles with a second particle composition comprising scaffolding particles;
wherein the carrier particles and targeting particles comprise poly(ethylene glycol)-poly(lactic-co-glycolic acid) copolymer and a collagen IV-targeting peptide; and the scaffolding particles comprise:
a core comprising poly(ethylene glycol)-poly(lactic-co-glycolic acid) copolymer; and
a shell, wherein the surface of the scaffolding particles comprise at least one diazirine group.

16. A method of reducing peritoneal adhesions, wherein said peritoneal adhesions form subsequent to abdominal surgery, said method comprising:
- contacting an abdominal surgical site with targeting particles;
- contacting said targeting particles with scaffolding particles; wherein the targeting particles comprise poly(ethylene glycol)-poly(lactic-co-glycolic acid) copolymer and a collagen IV-targeting peptide; and the scaffolding particles comprise:
  - a core comprising poly(ethylene glycol)-poly(lactic-co-glycolic acid) copolymer; and
  - a shell, wherein the surface of the scaffolding particles comprise at least one diazirine group; and
- UV induced crosslinking the targeting particles and scaffolding particles to provide a composite membrane at the abdominal surgical site, wherein said peritoneal adhesions are reduced by said composite membrane.

17. A method of reducing peritoneal adhesions, wherein said peritoneal adhesions form subsequent to abdominal surgery, said method comprising:
- contacting an abdominal surgical site with carrier particles;
- contacting said carrier particles with scaffolding particles; wherein the carrier particles comprise poly(ethylene glycol)-poly(lactic-co-glycolic acid) copolymer and a collagen IV-targeting peptide; and the scaffolding particles comprise:
  - a core comprising poly(ethylene glycol)-poly(lactic-co-glycolic acid) copolymer; and
  - a shell, wherein the surface of the scaffolding particles comprise at least one diazirine group; and
- UV induced crosslinking the carrier particles and scaffolding particles to provide a composite membrane at the abdominal surgical site, wherein said peritoneal adhesions are reduced by said composite membrane.

* * * * *